US011954470B2

(12) United States Patent
Jain et al.

(10) Patent No.: US 11,954,470 B2
(45) Date of Patent: Apr. 9, 2024

(54) ON-DEMAND DECENTRALIZED COLLECTION OF CLINICAL DATA FROM DIGITAL DEVICES OF REMOTE PATIENTS

(71) Applicant: VigNet Incorporated, Fairfax, VA (US)

(72) Inventors: Praduman Jain, Fairfax, VA (US); Dave Klein, Oakton, VA (US); Neeta Jain, Fairfax, VA (US); Yue Cao, Vienna, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 17/882,697

(22) Filed: Aug. 8, 2022

(65) Prior Publication Data

US 2022/0382538 A1 Dec. 1, 2022

Related U.S. Application Data

(60) Continuation of application No. 17/036,426, filed on Sep. 29, 2020, now Pat. No. 11,467,813, which is a
(Continued)

(51) Int. Cl.
*G06F 8/60* (2018.01)
*G06F 3/04817* (2022.01)
(Continued)

(52) U.S. Cl.
CPC ............ *G06F 8/60* (2013.01); *G06F 3/04817* (2013.01); *G06F 3/04842* (2013.01); *G06F 8/61* (2013.01);
(Continued)

(58) Field of Classification Search
None
See application file for complete search history.

(56) References Cited

U.S. PATENT DOCUMENTS 5,545,186 A 8/1996 Olson et al.
5,547,878 A 8/1996 Kell
(Continued)

FOREIGN PATENT DOCUMENTS

CN 106384321 2/2017
EP 2851820 3/2015
(Continued)

OTHER PUBLICATIONS

Airwatch: "AirWatch Enterprise Mobility Management Demo," YouTube, Jul. 22, 2014, retrieved on May 3, 2017, retrieved from URL <https://www.youtube.com/watch?v=ucV1n4-tgk>, 1 page.
(Continued)

*Primary Examiner* — Marina Lee
(74) *Attorney, Agent, or Firm* — Fish & Richardson P.C.

(57) ABSTRACT

In some implementations, a user interface for designing a health management module is provided by a server system. The user interface identifies a plurality of health management templates. The server system initially receives data indicating a user input received through the user interface that selects one of the plurality of module templates. The server system also receives customization parameters that customize the selected module template for a particular organization. The server system then generates a customized health management module for the particular organization based on the selected template and the customization parameters. The server system finally publishes the customized health management module for the particular organization that includes instructions configuring an application provided by a third-party application store.

20 Claims, 12 Drawing Sheets

Related U.S. Application Data continuation of application No. 16/847,428, filed on Apr. 13, 2020, now Pat. No. 11,314,492, which is a continuation of application No. 15/858,165, filed on Dec. 29, 2017, now Pat. No. 10,705,816, which is a division of application No. 15/040,635, filed on Feb. 10, 2016, now Pat. No. 9,858,063.

(51) Int. Cl.
| | |
|---|---|
| *G06F 3/04842* | (2022.01) |
| *G06F 8/61* | (2018.01) |
| *G06F 8/70* | (2018.01) |
| *G16H 40/63* | (2018.01) |
| *G16H 40/67* | (2018.01) |
| *H04L 67/00* | (2022.01) |
| *H04L 67/01* | (2022.01) |
| *H04L 67/025* | (2022.01) |
| *H04L 67/06* | (2022.01) |
| *H04L 67/125* | (2022.01) |
| *H04L 67/53* | (2022.01) |
| *G06F 8/38* | (2018.01) |
| *G16H 10/20* | (2018.01) |
| *G16H 10/60* | (2018.01) |
| *G16H 40/40* | (2018.01) |
| *H04L 41/0803* | (2022.01) |

(52) U.S. Cl.
CPC .............. *G06F 8/70* (2013.01); *G16H 40/63* (2018.01); *G16H 40/67* (2018.01); *H04L 67/01* (2022.05); *H04L 67/025* (2013.01); *H04L 67/06* (2013.01); *H04L 67/125* (2013.01); *H04L 67/34* (2013.01); *H04L 67/53* (2022.05); *G06F 8/38* (2013.01); *G16H 10/20* (2018.01); *G16H 10/60* (2018.01); *G16H 40/40* (2018.01); *H04L 41/0803* (2013.01)

(56) References Cited

U.S. PATENT DOCUMENTS

| | | | |
|---|---|---|---|
| 6,029,144 | A | 2/2000 | Barrett et al. |
| 6,029,195 | A | 2/2000 | Herz |
| 6,321,172 | B1 | 11/2001 | Jakob et al. |
| 6,514,200 | B1 | 2/2003 | Khouri |
| 6,663,846 | B1 | 12/2003 | McCombs et al. |
| 6,879,970 | B2 | 4/2005 | Shiffman et al. |
| 7,054,782 | B2 | 5/2006 | Hartlaub |
| 7,251,609 | B1 | 7/2007 | McAlindon et al. |
| 7,415,447 | B2 | 8/2008 | Shiffman et al. |
| 7,752,059 | B2 | 7/2010 | Sweeney et al. |
| 7,809,802 | B2 | 10/2010 | Lerman et al. |
| 7,827,478 | B2 | 11/2010 | Farr et al. |
| 7,827,495 | B2 | 11/2010 | Bells et al. |
| 7,853,455 | B2 | 12/2010 | Brown |
| 7,953,613 | B2 | 5/2011 | Gizewski |
| 8,056,100 | B2 | 11/2011 | Herz et al. |
| 8,065,180 | B2 | 11/2011 | Hufford et al. |
| 8,078,956 | B1 | 12/2011 | Feldman |
| 8,180,688 | B1 | 5/2012 | Velummylum et al. |
| 8,224,959 | B2 * | 7/2012 | Kirwan .................. H04L 43/00 709/224 |
| 8,239,918 | B1 | 8/2012 | Cohen |
| 8,302,020 | B2 | 10/2012 | Louch et al. |
| 8,347,263 | B1 | 1/2013 | Offer |
| 8,380,531 | B2 | 2/2013 | Paty et al. |
| 8,433,605 | B2 | 4/2013 | Hufford et al. |
| 8,533,029 | B2 | 9/2013 | Hufford et al. |
| 8,566,175 | B1 | 10/2013 | Nguyen et al. |
| 8,584,082 | B2 | 11/2013 | Baird et al. |
| 8,667,487 | B1 | 3/2014 | Boodman et al. |
| 8,775,415 | B2 | 7/2014 | Jeon et al. |
| 8,799,666 | B2 | 8/2014 | Kesanupalli et al. |
| 8,805,759 | B1 | 8/2014 | Cha et al. |
| 8,850,304 | B2 | 9/2014 | Ye et al. |
| 8,978,106 | B2 | 3/2015 | Swamy et al. |
| 8,990,250 | B1 | 3/2015 | Chowdry et al. |
| 8,997,038 | B2 | 3/2015 | Becker |
| 9,134,964 | B2 | 9/2015 | Hirsch |
| 9,135,445 | B2 | 9/2015 | Kay et al. |
| 9,170,800 | B2 | 10/2015 | Lang |
| 9,183,365 | B2 | 11/2015 | Taveau et al. |
| 9,256,698 | B2 | 2/2016 | Vincent, III |
| 9,361,011 | B1 | 6/2016 | Burns |
| 9,426,433 | B1 | 8/2016 | Mazzarella |
| 9,461,972 | B1 | 10/2016 | Mehta |
| 9,542,649 | B2 | 1/2017 | Su |
| 9,715,370 | B2 | 7/2017 | Friedman |
| 9,753,618 | B2 | 9/2017 | Jain |
| 9,760,343 | B2 | 9/2017 | Noens et al. |
| 9,824,606 | B2 | 11/2017 | Basson et al. |
| 9,848,061 | B1 | 12/2017 | Jain et al. |
| 9,858,063 | B2 | 1/2018 | Jain et al. |
| 9,928,230 | B1 | 3/2018 | Jain et al. |
| 9,940,454 | B2 | 4/2018 | Richardson et al. |
| 9,942,358 | B2 | 4/2018 | Babu et al. |
| 10,002,199 | B2 | 6/2018 | Matamala et al. |
| 10,007,501 | B1 | 6/2018 | Zhang et al. |
| 10,068,270 | B1 | 9/2018 | Kay et al. |
| 10,068,422 | B2 | 9/2018 | Gadher et al. |
| 10,069,934 | B2 | 9/2018 | Jain et al. |
| 10,095,688 | B1 | 10/2018 | Jain et al. |
| 10,152,761 | B2 | 12/2018 | Kress et al. |
| 10,202,769 | B2 | 2/2019 | Gya |
| 10,205,769 | B2 | 2/2019 | Sehgal |
| 10,248,401 | B1 | 4/2019 | Chen et al. |
| 10,304,000 | B2 | 5/2019 | Birnbaum et al. |
| 10,311,478 | B2 | 6/2019 | Dai et al. |
| 10,482,135 | B2 | 11/2019 | Rychikhin |
| 10,521,557 | B2 | 12/2019 | Jain et al. |
| 10,565,894 | B1 | 2/2020 | Jain et al. |
| 10,705,816 | B2 | 7/2020 | Jain et al. |
| 10,733,116 | B2 | 8/2020 | Litichever et al. |
| 10,733,266 | B2 | 8/2020 | Whitehurst |
| 10,756,957 | B2 | 8/2020 | Jain et al. |
| 10,762,990 | B1 | 9/2020 | Jain et al. |
| 10,775,974 | B2 | 9/2020 | Schilling et al. |
| 10,938,651 | B2 | 3/2021 | Jain et al. |
| 11,056,242 | B1 | 7/2021 | Jain et al. |
| 11,061,798 | B1 | 7/2021 | Jain et al. |
| 11,082,487 | B1 | 8/2021 | Jain et al. |
| 11,102,304 | B1 | 8/2021 | Jain et al. |
| 11,520,466 | B1 | 12/2022 | Schilling et al. |
| 2002/0022973 | A1 | 2/2002 | Sun |
| 2002/0035486 | A1 | 3/2002 | Huyn et al. |
| 2002/0099570 | A1 | 7/2002 | Knight |
| 2002/0143595 | A1 | 10/2002 | Frank et al. |
| 2002/0157091 | A1 | 10/2002 | DeMello et al. |
| 2003/0065669 | A1 | 4/2003 | Kahn et al. |
| 2003/0078960 | A1 | 4/2003 | Murren et al. |
| 2003/0130871 | A1 | 7/2003 | Rao et al. |
| 2003/0229522 | A1 | 12/2003 | Thompson et al. |
| 2004/0073868 | A1 | 4/2004 | Easter et al. |
| 2004/0122715 | A1 | 6/2004 | McAuliffe |
| 2004/0172447 | A1 | 9/2004 | Miller |
| 2004/0210457 | A1 | 10/2004 | Sameh |
| 2005/0050320 | A1 | 3/2005 | Wassmann et al. |
| 2005/0055687 | A1 | 3/2005 | Mayer |
| 2005/0071752 | A1 | 3/2005 | Marlatt |
| 2005/0086587 | A1 | 4/2005 | Balz |
| 2005/0144072 | A1 | 6/2005 | Perkowski et al. |
| 2005/0165626 | A1 | 7/2005 | Karpf |
| 2006/0004603 | A1 | 1/2006 | Peterka et al. |
| 2006/0184493 | A1 | 8/2006 | Shiffman et al. |
| 2006/0205564 | A1 | 9/2006 | Peterson |
| 2006/0282516 | A1 | 12/2006 | Taylor |
| 2007/0072156 | A1 | 3/2007 | Kaufman et al. |
| 2007/0136093 | A1 | 6/2007 | Rankin et al. |
| 2007/0179361 | A1 | 8/2007 | Brown et al. |
| 2007/0250429 | A1 | 10/2007 | Walser et al. |
| 2008/0005679 | A1 | 1/2008 | Rimas-Ribikauskas |
| 2008/0010254 | A1 | 1/2008 | Settimi |

(56) References Cited

U.S. PATENT DOCUMENTS

| | | |
|---|---|---|
| 2008/0021287 A1 | 1/2008 | Woellenstein et al. |
| 2008/0034314 A1 | 2/2008 | Louch et al. |
| 2008/0126110 A1 | 5/2008 | Haeberle |
| 2008/0127040 A1 | 5/2008 | Barcellona |
| 2008/0140444 A1 | 6/2008 | Karkanias |
| 2009/0024944 A1 | 1/2009 | Louch |
| 2009/0043689 A1 | 2/2009 | Yang |
| 2009/0094052 A1 | 4/2009 | James et al. |
| 2009/0119678 A1 | 5/2009 | Shih |
| 2009/0156190 A1 | 6/2009 | Fisher |
| 2009/0163182 A1 | 6/2009 | Gatti |
| 2009/0172002 A1 | 7/2009 | Bathiche |
| 2009/0248883 A1 | 10/2009 | Suryanarayana et al. |
| 2010/0036681 A1 | 2/2010 | Naik et al. |
| 2010/0041378 A1 | 2/2010 | Aceves |
| 2010/0088245 A1 | 4/2010 | Harrison et al. |
| 2010/0131482 A1 | 5/2010 | Linthicum |
| 2010/0211941 A1 | 8/2010 | Roseborough |
| 2010/0218132 A1 | 8/2010 | Soni et al. |
| 2010/0235889 A1 | 9/2010 | Chu et al. |
| 2010/0250258 A1 | 9/2010 | Smithers et al. |
| 2011/0066934 A1 | 3/2011 | Treisman |
| 2011/0145747 A1 | 6/2011 | Wong et al. |
| 2011/0166628 A1 | 7/2011 | Jain |
| 2011/0167133 A1* | 7/2011 | Jain .................... H04L 67/12 709/219 |
| 2011/0173308 A1 | 7/2011 | Gutekunst |
| 2011/0200979 A1 | 8/2011 | Benson |
| 2011/0288900 A1 | 11/2011 | McQueen et al. |
| 2012/0035954 A1 | 2/2012 | Yeskel |
| 2012/0047029 A1 | 2/2012 | Veres et al. |
| 2012/0072232 A1 | 3/2012 | Frankham et al. |
| 2012/0084399 A1 | 4/2012 | Scharber et al. |
| 2012/0089521 A1 | 4/2012 | Abrevaya et al. |
| 2012/0102050 A1 | 4/2012 | Button |
| 2012/0143694 A1 | 6/2012 | Zargahi |
| 2012/0143697 A1 | 6/2012 | Chopra |
| 2012/0272156 A1 | 10/2012 | Kerger |
| 2013/0085744 A1 | 4/2013 | Arias |
| 2013/0103749 A1 | 4/2013 | Werth et al. |
| 2013/0110565 A1 | 5/2013 | Means |
| 2013/0145024 A1 | 6/2013 | Cao |
| 2013/0166494 A1 | 6/2013 | Davis |
| 2013/0179472 A1 | 7/2013 | Junqua |
| 2013/0238686 A1 | 9/2013 | O'Donoghue |
| 2013/0283188 A1 | 10/2013 | Sanghvi |
| 2013/0326375 A1 | 12/2013 | Barak et al. |
| 2014/0017648 A1 | 1/2014 | Williams et al. |
| 2014/0019480 A1 | 1/2014 | Rychikhin |
| 2014/0026113 A1 | 1/2014 | Farooqi |
| 2014/0033171 A1 | 1/2014 | Lorenz |
| 2014/0052681 A1 | 2/2014 | Nitz et al. |
| 2014/0088995 A1 | 3/2014 | Damani |
| 2014/0100883 A1 | 4/2014 | Hamilton |
| 2014/0101628 A1 | 4/2014 | Almog |
| 2014/0109072 A1 | 4/2014 | Lang et al. |
| 2014/0109115 A1 | 4/2014 | Low |
| 2014/0109177 A1 | 4/2014 | Barton et al. |
| 2014/0156645 A1 | 6/2014 | Brust |
| 2014/0156823 A1 | 6/2014 | Liu |
| 2014/0157171 A1 | 6/2014 | Brust et al. |
| 2014/0173405 A1 | 6/2014 | Ferrara |
| 2014/0181715 A1 | 6/2014 | Axelrod |
| 2014/0187228 A1 | 7/2014 | Fisher |
| 2014/0240122 A1 | 8/2014 | Roberts |
| 2014/0257058 A1 | 9/2014 | Clarysse et al. |
| 2014/0258827 A1 | 9/2014 | Gormish |
| 2014/0273913 A1 | 9/2014 | Michel |
| 2014/0278536 A1 | 9/2014 | Zhang |
| 2014/0288955 A1 | 9/2014 | Zhou et al. |
| 2014/0317595 A1 | 10/2014 | Kilby |
| 2014/0344397 A1 | 11/2014 | Kostof |
| 2014/0358482 A1 | 12/2014 | Sehgal |
| 2014/0365961 A1 | 12/2014 | Lefor et al. |
| 2015/0006214 A1 | 1/2015 | Lavoie et al. |
| 2015/0012301 A1 | 1/2015 | Weschler et al. |
| 2015/0074635 A1 | 3/2015 | Margiotta |
| 2015/0088955 A1 | 3/2015 | Hendrick et al. |
| 2015/0089224 A1 | 3/2015 | Beckman |
| 2015/0106449 A1 | 4/2015 | Cherry |
| 2015/0135160 A1 | 5/2015 | Gauvin |
| 2015/0148061 A1 | 5/2015 | Koukoumidis |
| 2015/0163121 A1 | 6/2015 | Mahaffey |
| 2015/0178473 A1 | 6/2015 | Hufford et al. |
| 2015/0178474 A1 | 6/2015 | Hufford et al. |
| 2015/0212714 A1 | 7/2015 | Hua |
| 2015/0213197 A1 | 7/2015 | Brennan et al. |
| 2015/0220233 A1 | 8/2015 | Kok et al. |
| 2015/0286802 A1 | 10/2015 | Kansara |
| 2015/0294090 A1 | 10/2015 | Kodiyan |
| 2015/0347784 A1* | 12/2015 | Keen .................... G06F 21/6245 726/28 |
| 2016/0021040 A1 | 1/2016 | Frei |
| 2016/0058287 A1 | 3/2016 | Dyell |
| 2016/0085754 A1 | 3/2016 | Gifford et al. |
| 2016/0092339 A1 | 3/2016 | Straub |
| 2016/0124930 A1 | 5/2016 | Dhawan |
| 2016/0196389 A1 | 7/2016 | Moturu et al. |
| 2016/0203663 A1 | 7/2016 | Proctor |
| 2016/0217118 A1 | 7/2016 | Singh |
| 2016/0234624 A1 | 8/2016 | Riva et al. |
| 2016/0300570 A1 | 10/2016 | Gustafson et al. |
| 2016/0357794 A1 | 12/2016 | Liang et al. |
| 2016/0357944 A1 | 12/2016 | Iyer et al. |
| 2017/0000422 A1 | 1/2017 | Moturu et al. |
| 2017/0024546 A1 | 1/2017 | Schmidt |
| 2017/0039324 A1 | 2/2017 | Francois et al. |
| 2017/0048215 A1 | 2/2017 | Straub |
| 2017/0049374 A1 | 2/2017 | Eldardiry et al. |
| 2017/0097743 A1 | 4/2017 | Hameed et al. |
| 2017/0124276 A1 | 5/2017 | Tee |
| 2017/0132395 A1 | 5/2017 | Futch |
| 2017/0132396 A1 | 5/2017 | Bechtold et al. |
| 2017/0169343 A1 | 6/2017 | Kirkham et al. |
| 2017/0118159 A1 | 7/2017 | Ratiu et al. |
| 2017/0228229 A1 | 8/2017 | Jain et al. |
| 2017/0231528 A1 | 8/2017 | Nathan |
| 2017/0249435 A1* | 8/2017 | Lancelot .............. G06F 21/6245 |
| 2017/0286389 A1 | 10/2017 | Ceneviva |
| 2017/0286605 A1 | 10/2017 | Wong et al. |
| 2017/0308680 A1 | 10/2017 | Efros et al. |
| 2017/0329483 A1 | 11/2017 | Jann et al. |
| 2017/0329500 A1 | 11/2017 | Grammatikakis et al. |
| 2017/0330297 A1 | 11/2017 | Cronin et al. |
| 2017/0344895 A1 | 11/2017 | Roy |
| 2017/0374178 A1 | 12/2017 | Sharma et al. |
| 2018/0046780 A1 | 2/2018 | Graiver et al. |
| 2018/0089159 A1 | 3/2018 | Jain et al. |
| 2018/0090229 A1 | 3/2018 | Sanyal |
| 2018/0114596 A1 | 4/2018 | Churchwell et al. |
| 2018/0121187 A1 | 5/2018 | Jain et al. |
| 2018/0122509 A1 | 5/2018 | Christiansson |
| 2018/0150523 A1 | 5/2018 | Shiffman et al. |
| 2018/0176331 A1 | 6/2018 | Jain et al. |
| 2018/0206775 A1 | 7/2018 | Saria et al. |
| 2018/0210870 A1 | 7/2018 | Jain et al. |
| 2018/0286509 A1 | 10/2018 | Shah |
| 2018/0341378 A1 | 11/2018 | Morrow |
| 2018/0365316 A1 | 12/2018 | Liang et al. |
| 2019/0026663 A1 | 1/2019 | Homeyer et al. |
| 2019/0068753 A1 | 2/2019 | Jain et al. |
| 2019/0207814 A1 | 7/2019 | Jain |
| 2019/0306093 A1 | 10/2019 | Schilling et al. |
| 2019/0361579 A1 | 11/2019 | Srivastava |
| 2020/0035341 A1 | 1/2020 | Kain et al. |
| 2020/0050330 A1 | 2/2020 | Schilling et al. |
| 2020/0131581 A1 | 4/2020 | Jain et al. |
| 2020/0203012 A1 | 6/2020 | Kamath et al. |
| 2020/0241859 A1 | 7/2020 | Jain et al. |
| 2020/0241860 A1 | 7/2020 | Jain et al. |
| 2020/0243167 A1 | 7/2020 | Will et al. |
| 2020/0250508 A1 | 8/2020 | De Magalhaes |
| 2020/0267110 A1 | 8/2020 | Nolan et al. |
| 2020/0278852 A1 | 9/2020 | Jain et al. |

(56) References Cited

U.S. PATENT DOCUMENTS

| | | | |
|---|---|---|---|
| 2020/0303074 A1 | 9/2020 | Mueller-Wolf | |
| 2020/0336450 A1 | 10/2020 | Gao et al. | |
| 2020/0348919 A1 | 11/2020 | Jain | |
| 2021/0058490 A1 | 2/2021 | Jain | |

FOREIGN PATENT DOCUMENTS

| | | |
|---|---|---|
| WO | WO1995012812 | 5/1995 |
| WO | WO2012078753 | 6/2012 |
| WO | WO2013144769 | 10/2013 |

OTHER PUBLICATIONS

Airwatch: "Airwatch Laptop Management Demo," YouTube, Oct. 3, 2014, retrieved on May 3, 2017, retrieved from URL<https://www.youtube.com/watch?v=3gHfmdVZECM>, 1 page.
alphr.com [online], "How to Write A Chrome Extension", published on Nov. 22, 2010, retrieved on Oct. 18, 2021, retrieved from URL<https://www.alphr.com/tutorials/363031/how-to-write-a-chrome-extension/>, 12 pages.
ditoweb.com [online], "What is the Google Chrome Web Store?", published in Aug. 2012, retrieved on Oct. 18, 2021, retrieved from URL<https://www.ditoweb.com/2012/08/what-is-google-chrome-web-store/>, 8 pages.
edsurge.com [online], "Extensions, Add-Ons and Apps, Oh My! How to Utilize Google in Your Classroom", published on Oct. 13, 2014, retrieved on Oct. 18, 2021, retrieved from URL<https://www.edsurge.com/news/2014-10-13-extensions-add-ons-and-apps-oh-my-how-to-utilize-google-in-your-classroom>, 5 pages.
EP Search Report in European Appln. No. 17706938.2, dated Nov. 6, 2019, 7 pages.
Final Office Action in U.S. Appl. No. 15/040,635, dated Apr. 13, 2017, 13 pages.
Final Office Action in U.S. Appl. No. 15/858,165, dated Nov. 6, 2019, 13 pages.
Final Office Action in U.S. Appl. No. 17/076,056, dated Jan. 21, 2022, 38 pages.
ghacks.net [online], "The Best Way to Find New Extensions on the Chrome Web Store", published on May 12, 2014, retrieved on Oct. 18, 2021, retrieved from URL<https://www.ghacks.net/2014/05/12/best-way-find-new-extensions-chrome-web-store/>, 6 pages.
Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.
groovypost.com [online], "How Safe is it to Download Chrome Extensions", published on Mar. 4, 2011, retrieved on Oct. 18, 2021, retrieved from URL<https://www.groovypost.com/howto/reviews/chrome-extensions-privacy-security/>, 7 pages.
Guyot, "Apple's ResearchKit: Our Complete Overview," Mar. 9, 2015, retrieved on Mar. 30, 2020, retrieved from URL<https://www.macstories.net/news/apples-researchkit-our-complete-overview/>, 8 pages.
Henze et al., "Push the study to the App store: evaluating off-screen visualizations for maps in the android market," Proceedings of the 12th Conference on Human-Computer Interaction with Mobile Devices and Services, Lisbon, Portugal, Sep. 7-10, 2010, 373-374. http://www.khanacademic.org, 2017, 1 page.
Kotsiantis, "Supervised Machine Learning: A Review of Classification Techniques", Informatica 31, Jul. 2007, pp. 249-268.
Lunn et al., "Using Mobile Technology to Engage Sexual and Gender Minorities in Clinical Research," PLOS ONE, May 2, 2019, 14(5), 19 pages.
makeuseof.com [online], "How Safe Is The Chrome Web Store Anyway?", published on Apr. 10, 2015, retrieved on Oct. 18, 2021, retrieved from URL<https://www.makeuseof.com/tag/secure-chrome-web-store-anyway/>, 16 pages.
Matthews, "Johns Hopkins Researchers to Use Apple Watch Data to Study Epilepsy," Oct. 15, 2015, retrieved on Mar. 30, 2020, retrieved from URL<https://hub.jhu.edu/2015/10/15/apple-watch-epi-watch/>, 3 pages.
Non-Final Office Action in U.S. Appl. No. 15/040,635, dated Dec. 30, 2016, 11 pages.
Non-Final Office Action in U.S. Appl. No. 15/040,635, dated Jul. 8, 2016, 9 pages.
Non-Final Office Action in U.S. Appl. No. 15/279,845, dated Apr. 21, 2017, 10 pages.
Non-Final Office Action in U.S. Appl. No. 15/337,222, dated Mar. 23, 2017, 13 pages.
Non-Final Office Action in U.S. Appl. No. 15/382,126, dated Mar. 17, 2017, 16 pages.
Non-Final Office Action in U.S. Appl. No. 15/858,165, dated Apr. 3, 2019, 14 pages.
Non-Final Office Action in U.S. Appl. No. 16/847,428, dated Sep. 15, 2020, 13 pages.
Non-Final Office Action in U.S. Appl. No. 16/847,452, dated Sep. 16, 2020, 13 pages.
Non-Final Office Action in U.S. Appl. No. 16/877,187, dated Jul. 20, 2020, 23 pages.
Non-Final Office Action in U.S. Appl. No. 16/877,187, dated May 5, 2021, 28 pages.
Non-Final Office Action in U.S. Appl. No. 16/942,822, dated Jul. 21, 2021, 22 pages.
Non-Final Office Action in U.S. Appl. No. 17/036,426, dated Aug. 3, 2021, 23 pages.
Non-Final Office Action in U.S. Appl. No. 17/244,131, dated Jan. 19, 2022, 30 pages.
Notice of Allowance in U.S. Appl. No. 16/847,428, dated Jan. 5, 2021, 17 pages.
Notice of Allowance in U.S. Appl. No. 16/877,187, dated Sep. 22, 2021, 8 pages.
Obgyn.com [online], "Neural Networks", published in 2002, retrieved on Jan. 19, 2021, 34 pages.
PCT International Preliminary Report on Patentability in International Appln No. PCT/US2017/017480, dated Aug. 23, 2018, 13 pages.
PCT International Search Report and Written Opinion in International Appln. No. PCT/US2017/017480, dated May 17, 2017, 19 pages.
Pogue, "Apple's First 5 Health ResearchKit Apps in Brief," Jul. 1, 2015, retreived on Mar. 30, 2020, retrieved from URL<https://www.scientificamerican.com/article/pogue-apples-first-5-health-researchkit-apps-in-brief/>, 4 pages.
Rabelo et al., "Development of a real-time learning scheduler using reinforcement learning concepts", Proceedings of the 1994 9th IEEE International Symposium on Intelligent Control, 1994, pp. 291-296.
sbir.cancer.gov [online], "322 Real-Time Integration of Sensor and Self-Report Data for Clinical and Research Applications", published on Jun. 24, 2015, retrieved on Oct. 18, 2021, retrieved from URL<https://sbir.cancer.gov/funding/contracts/pastcontracts/322>, 3 pages.
sbir.cancer.gov [online], "340 Validation of Mobile Technologies for Clinical Assessment, Monitoring and Intervention", published on Jun. 24, 2015, retrieved on Oct. 18, 2021, retrieved from URL<https://sbir.cancer.gov/funding/contracts/pastcontracts/340>, 3 pages.
sbir.cancer.gov [online], "NIH/NCI 342: Validation of Mobile Technologies for Clinical Assessment, Monitoring and Intervention", published on Jul. 24, 2015, retrieved on Oct. 24, 2015, retrieved from URL<https://sbir.cancer.gov/funding/contracts/nihnci342>, 4 pages.
sitepoint.com [online], "How to Create a Chrome Extension in 10 Minutes Flat", published on Apr. 8, 2015, retrieved on Oct. 18, 2021, retrieved from URL<https://www.sitepoint.com/create-chrome-extension-10-minutes-flat/>, 11 pages.
smallbusiness.chron.com [online], "What Is The Chrome Web Store", published on Oct. 6, 2011, retrieved on Oct. 18, 2021, retrieved from URL<https://smallbusiness.chron.com/chrome-store-26652.html>, 5 pages.

(56) References Cited

OTHER PUBLICATIONS

Taivan et al., "Application Diversity in Open Display Networks," Proceedings of the International Symposium on Pervasive Displays, Copenhagen, Denmark, Jun. 2014, 68-73.

techcrunch.com [online], "Google Gives Chrome Web Store a Welcome New Lick of Paint", published on Oct. 15, 2011, retrieved on Oct. 18, 2021, retrieved from URL<https://techcrunch.com/2011/10/25/google-gives-chrome-web-store-a-welcome-new-lick-of-paint/>, 8 pages.

web.archive.com [online], "Extension Templates and Samples", published on Jul. 15, 2020, retrieved on Oct. 18, 2021, retrieved from URL<https://web.archive.org/web/20200715011834/https:/dev.opera.com/extensions/extension-samples/>, 5 pages.

Non-Final Office Action in U.S. Appl. No. 17/968,442, dated Jan. 26, 2024, 43 pages.

\* cited by examiner

ON-DEMAND DECENTRALIZED COLLECTION OF CLINICAL DATA FROM DIGITAL DEVICES OF REMOTE PATIENTS

CROSS-REFERENCE TO RELATED APPLICATIONS

This application is a continuation of U.S. application Ser. No. 17/036,426, filed Sep. 29, 2020, which is a continuation of U.S. application Ser. No. 16/847,428, filed Apr. 13, 2020, now U.S. Pat. No. 11,314,492, which is a continuation of U.S. application Ser. No. 15/858,165, filed Dec. 29, 2017, now U.S. Pat. No. 10,705,816, which is a divisional of U.S. application Ser. No. 15/040,635, filed Feb. 10, 2016, now U.S. Pat. No. 9,858,063. The entire contents of each of the prior applications are incorporated by reference.

GOVERNMENT LICENSE RIGHTS

This invention was made with government support under grant number HHSN261201300056C awarded by the National Institutes of Health. The government has certain rights in the invention.

FIELD

This specification generally describes technology related to publishing customized application modules.

BACKGROUND

Applications for computers, mobile devices, and other devices can provide useful functionality to users. However, it can be very costly and time consuming to create, distribute, and maintain an application.

Typically, it is very difficult for organizations to create and distribute mobile applications and other solutions that can meet the needs of their members. Different organizations have widely varying health policies. For example, different organizations may have different insurance options and health goals for their members. Similarly, individuals have widely varying healthcare needs.

SUMMARY

In some implementations, a system provides a platform that allows efficient creation and distribution of customized program modules to users. Individual users can download a single application from a server for an application store or marketplace. Separately, a publishing system provides modules for the application that define different sets of functionality and different user experiences. Various organizations can use the publishing system to quickly create and customize a program module to meet their needs, based on predetermined templates offered by the publishing system. For example, the publishing system allows an organization to customize the module templates to use the organization's own name, logo, media, and other branding assets. Organizations can also select which aspects of the application will be made available to the user and in what manner. By creating a custom module, an organization can define a unique, branded user experience for an application, e.g., for a mobile device such as a smartphone or tablet computer, without requiring the organization to invest the time and effort to code, test, publish, and maintain an application.

When a user downloads and installs the application associated with the publishing system, the user can select and download an appropriate customized module. The module can include a variety of elements that adjust the user's experience. For example, a module can include custom content from the organization that customized it, as well as interactive elements, media, and features from the template used to generate the module. After downloading the module, the application may reconfigure its interface as directed by the module, as if the organization that customized the module had provided the user a customized, stand-alone application.

In some implementations, organizations may use the publishing system to customize modules that enhance the wellbeing of users. For example, an organization may provide various modules that support health initiatives of a company. Using the publishing system, the employer may select module templates for various aspects of wellbeing, such as general fitness, weight loss, diabetes management, and so on. The module templates may include clinically validated information and recommendations tailored for a specific medical condition or health goal. This template information provides the employer effective, validated techniques to improve a user's health, without requiring the employer to invest in research to identify appropriate user experiences supporting health. The employer may customize the template, for example, specifying additional goals or incentives specific to the employer, as well as health insurance information that is applicable for the employer. Additionally, the employer may include the employer's name, logo, and other content, so that once the module is downloaded and incorporated into the application, the application may appear as if it were a fully customized application from the employer. In a similar manner, health insurance companies, doctors and hospitals, government entities, and other organizations may all create their own respective customized modules to be published.

In some implementations, customized health management modules can be used to provide organization-specific information on user interfaces of mobile applications from a third-party application store. The customized health management modules can be published by a publishing system that supports data collection and monitoring processes associated with health management programs provided by multiple healthcare providers. The customized health management modules can be used to integrate various types of information from different entities associated with healthcare services such as insurance companies, providers, pharmacies, and patients into a common platform with limited costs of implementation for organizations that provide modules through the publishing system.

In one general aspect, a computer-implemented method includes: providing, by a server system, a user interface for designing a health management module, the user interface identifying a plurality of health management module templates; receiving, by the server system, data indicating a user input received through the user interface that selects of one of the plurality of module templates; receiving, by the server system, customization parameters that customize the selected module template for a particular organization; generating, by the server system, a customized health management module for the particular organization based on the selected template and the customization parameters; and publishing, by the server system, the customized health management module for the particular organization, the customized health management module including instructions that configures an application provided by a third-party application store.

Implementations can include one or more optional features. For instance, in some implementations, each of the particular organization, an operator of the third-party application store, and the provider of the application are independent entities.

In some implementations, the plurality of health management module templates include multiple templates corresponding to different medical conditions, each of the multiple templates including clinical information for the corresponding medical condition.

In some implementations, the user interface for designing the health management module additionally identifies a set of interactivity settings.

In some implementations, the customization parameters specify one or more access conditions for the customized health management module for the particular organization.

In some implementations, the customization parameters include information identifying healthcare initiatives provided by the particular organization.

In some implementations, generating the customized health management module for the particular organization includes: identifying a module template based on user input; associating media content for the particular organization; and defining one or more user interaction settings for the customized health management module.

In some implementations, publishing the customized health management module for the particular organization includes providing the customized health management module over a network for access by the application provided by the third-party application store.

In some implementations, publishing the customized health management module for the particular organization includes: receiving, by the server system and from a client device having the application from the third party application store installed, a request for the customized health management module for the particular organization; and in response to receiving the request for the customized health management module for the particular organization, transferring, over a network, the customized health management module to the client device that has previously installed the application from the third-party application store such that the customized health management module performs a set of operations to adjust the application on the client device.

In some implementations, the customized health management module includes one or more tracking modules, the one or more tracking modules configured to initiate monitoring and reporting of predetermined content items associated with the application provided by the third party application store according to predetermined conditions specified by the customized health management module.

In some implementations, the customization parameters that customize the selected module template specify branding items, associated with the particular organization, to be displayed on the customized health management module.

In some implementations, the customization parameters that customize the selected module template specify interaction rules that specify techniques for submitting information on a user interface of the application provided by the third party application store.

In some implementations, generating the customized health management module for the particular organization includes: determining one or more healthcare providers that are supported by the particular organization to provide healthcare services; and generating the customized health management module to include information associated with the one or more healthcare providers that are supported by the particular organization to provide healthcare services.

In another general aspect, a computer-implemented method includes: installing, at an electronic device, an application downloaded over a computer network from an application store provided by a first server system; after installing the application, displaying, at the electronic device, a list of health management modules provided by a second server system that is independent of the first server system; providing, by the electronic device and to the second server system, data indicating one of the listed health management modules that was selected by a user of the electronic device; receiving, by the electronic device and from the second server system, the selected health management module; and installing, by the electronic device, the received health management module to modify the application to interact with the user according to the received health management module.

In some implementations, providing the data indicating one of the listed health management modules that was selected by the user of the electronic device includes information of a particular organization associated with the one of the listed health management modules that was selected by the user of the electronic device, and receiving the selected health management module includes receiving a list of health management modules that correspond to the particular organization.

In some implementations, installing the received health management module to modify the application includes: storing the received health management module on the electronic device; and designating the received health management module as a health management module to be displayed on the application during a subsequent application session.

In some implementations, modifying the application to interact with the user includes at least one of adjusting the user interface of the application, or adjusting tracking and reporting operations associated with the application.

In some implementations, the computer-implemented method for installing the received health management module includes modifying the application based on a set of instructions within the received health management module, the set of instructions enabling one or more functions of the application during a subsequent application session.

In some implementations, the application provided by the third-party application store is configured according to a local application configuration.

In some implementations, the computer-implemented method for installing the received health management module includes, after installing the received health management module, receiving, from the second server system, data indicating one or more updates to the received health management module.

The details of one or more implementations are set forth in the accompanying drawings and the description below. Other potential features and advantages will become apparent from the description, the drawings, and the claims.

BRIEF DESCRIPTION OF THE DRAWINGS

In the drawings, like reference numbers represent corresponding parts throughout.

DETAILED DESCRIPTION

Figure 1:
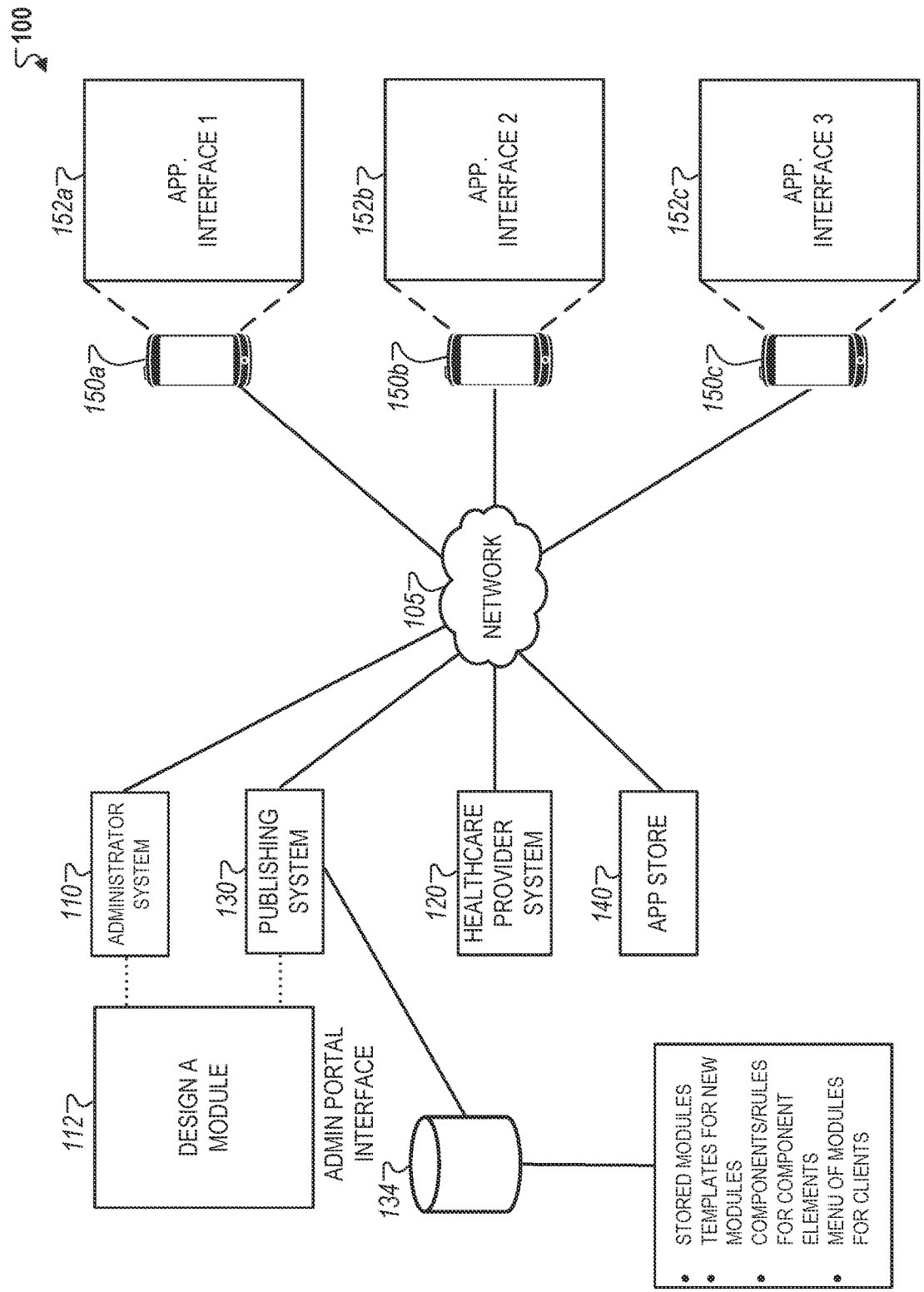
FIG. 1 is a diagram that illustrates an example of a publishing system.

In general, this specification describes systems and methods for generating and publishing customized program modules that adjust a user experience provided by an application. The customized module can include data that directs the application how to use and display various capabilities already existing in the application. In some implementations, the publishing system provides customized health management modules that enable client organizations to provide customized information to users through a single publishing platform. The publishing system allows client organizations to provide their members the benefits of customized applications without incurring the significant costs associated with developing and distributing a new application for each organization.

The publishing system can provide a publishing platform for generating and distributing customized health management modules. A client organization can use the publishing platform provided by the publishing system to distribute a health management module to users. In addition, a healthcare provider can also provide information that is used in the health management modules. Finally, a user can be an end-user that installs a mobile application from a third-party app store on a user device, and then downloads one of the customized health management modules provided by the publishing system.

As described herein, a "health management module" refers to a set of computer-implemented code or instructions that define a user experience associated with a mobile application. The health management module can indicate specific features of an application that a particular client organization selected to expose to the user. When downloaded and stored on a user device, the module configures the associated mobile application to provide custom content and interactions selected by the client organization. When the user subsequently runs the application, the application retains the configuration, appearance, and interactivity specified by the previously downloaded module. Using a customized module, the client organization can provide the user the experience of a native mobile application without the need for the client organization to code and register an application with an app store (e.g., the Apple App Store, or Google Play for Android Apps, etc.). The health management module can also include or refer to various content items such as media, forms, and user interface parameters that include customized logos and branding for a client organization. In addition, the health management module enables the user and the client organization to perform specific types of data tracking and reporting according to a user's specific medical needs, or the priorities of the client organization (e.g., to encourage and reward exercise, or to promote quitting smoking, etc.). In this regard, the health management module can be customized to the goals of the client organization, the user, or both.

Several different actors interact with the publishing system, for example, (a) a "client organization," (b) an "administrator," (c) a "healthcare provider," and (d) a "user" (or "patient"). A "client organization" refers to an organization that uses the services of the publishing system to distribute a module for the organization. For instance, the client organization can be an employer that provide healthcare insurance or other health management programs to employees. When using the publishing system, the client organization can provide organization-specific information such as logos, promotional content, or specific healthcare initiatives to the publishing system to display to users that use the customized module.

An "administrator" refers to an entity or individual that interacts with an administrator portal of the publishing system to create a customized healthcare module. In some instances, the administrator is an employee or representative of the client organization that manages and updates the customized module. For instance, the administrator can use an administrator portal of the publishing system to select from various options and provide specifications for a desired module. Additionally, the administrator may identify a list of users that are eligible to receive the module, data indicating applicable healthcare providers or insurance plans, access privileges associated with particular features of the health management modules, or custom content for health management modules.

A "healthcare provider" refers to individuals, institutions, or organizations that provide healthcare services to users. In some instances, the healthcare provider can be an individual health professional such as a physician, or an entity such as a hospital that provides preventative, curative, or rehabilitative programs for users, or a health insurance provider. Healthcare providers can use a provider portal to interact with the publishing system, both to submit information that is accessed through appropriate modules and to receive information from users of certain modules to use in enhancing treatment. As an example, healthcare providers may submit health-related information such as electronic health records, treatment program information, or promotional material. This information may be general for a group of users (e.g., for all users who have a particular insurance plan) or specific to individual users. In some instances, the information submitted on the provider portal can be compiled into a set of module information that is used to personalize the display and operation of the customized health management modules to the provider.

A "user" or "patient" refers to an individual that uses a mobile application and one or more customized modules. In some instances, the user receives healthcare-related services from the healthcare provider. For instance, the user can use a mobile application that is customized using a healthcare module created on behalf of the user's employer, the user's insurance company, or another entity.

FIG. 1 is a diagram that illustrates an example of a publishing system 100. The system 100 can include an administrator system 110, a healthcare provider system 120, a publishing system 130, an app store 140, and one or more user devices 150a, 150b, 150c connected over a network 105. The administrator system 110 can access an admin portal 112 provided by the publishing system 130. The publishing system 130 can include a repository 134 for storing content and information associated with the publishing system 100, such as templates for creating new modules and previously-created custom modules and associated content. In addition, each of the user devices 150a, 150b, and 150c can display user interfaces 152a, 152b, and 152c, respectively, to a set of different users associated with each of the user devices.

In more detail, the administrator system 110 can be a computing system used by an administrator of a client organization that uses the publishing system 130 to create and distribute a customized module. The administrator system 110 can access an administrator portal 112 that is provided by the publishing system 130. The administrator portal 112 can be used by the administrator to create or update a set of module specifications that configure a health management modules for a specific client organization. In addition, the administrator portal 112 can be used to identify which users are eligible for the customized module. Also, the admin portal can also be used to configure a payment gateway that is used in financial transactions associated with the client organization.

The admin portal 112 can also be used to create accounts for providers that are associated with a client organization. For example, the providers can be healthcare insurers and/or healthcare providers that accept the health insurance plans that are provided to employees of the client organization.

The healthcare provider system 120 can be a computing system that includes information related to one or more healthcare providers. The healthcare provider system 120 can access a provider portal provided by the publishing system 130 to submit patient and provider information that is relevant to treatment programs created in the admin portal 112. For example, a provider can submit medical histories, immunization records, previous consultation reports, and/or procedure charts for a particular user through the provider portal, which can then be associated with specific treatment programs for the particular user. In addition, the provider portal can be used by providers to periodically update patient and provider information such that the data within the application ecosystem of the system 110 is up-to-date and accurate.

The publishing system 130 can be a remote server that aggregates information provided by administrators on the admin portal 112 and by providers on the healthcare provider portal 122, and generates customized health management modules based on the information provided. For instance, as described more particularly with respect to FIG. 2A, the publishing system 130 can use the module specifications received from the admin portal and the module information received from the healthcare provider portal 122 to generate customization instructions that customize a module for a particular organization. The publishing system 130 also includes the repository 134, which can store related information of the system 100. For example, as depicted in FIG. 1, the repository 134 can include stored modules for other client organizations, templates for new health management modules, components or rules for components or elements to be included within health management modules, or lists of available modules for the user.

The app store 140 can be a mobile application store associated with the particular operating system of the user devices 150a, 150b, and 150c. The app store 140 can be operated by an entity that is independent of the client organization and its associated administrator, the healthcare provider, and the publishing system. In particular, an application associated with the publishing system may be provided by a server for an app store, but the publishing system 130 may independently provide modules that are subsequently downloaded after the application is installed. For instance, the app store 140 can be operated by a third party mobile device manufacturer or a third party software vendor that provides software development toolkits to design mobile applications on the mobile operating systems of the user devices 150a, 150b, 150c. Examples of app stores include the Apple App Store, the Google Play app store for Android devices, and the Amazon.com app store. In some instances, different app stores 140 can be used with different mobile operating systems of the user devices 150b, and 150c. In such instances, a mobile application of the publishing system 100 can be designed for multiple mobile operating systems.

The app store 140 can be used by users to install a mobile application associated with the system 100 onto the user devices 150a, 150b, and 150c. For instance, the same mobile application can display the interfaces 152a, 152b, and 152c to users of the user devices 150a, 150b, and 150c. In addition, as described more particularly with respect to FIG. 2A, the mobile application can periodically receive data from the publishing system 130 that include instructions to adjust the interfaces 152a, 152b, and 152c according to the customized health management modules. The instructions can different for each user device, according to the different modules installed, the different healthcare providers associated, and the user's individual health needs. As a result, the interfaces 152a, 152b, and 152c may provide information tailored for each user's organization, and in some instances, user-specific information.

The user devices 150a, 150b, 150c can be any type of electronic device that is capable of running third party mobile applications from the app store 140. For instance, the user devices 150a, 150b, 150c can be one or more of a smart phone, a laptop computing device, a tablet computing device, a watch or other connected wearable device, or other types of network-enabled computing devices. In addition, the user devices 150a, 150b, 150c can be associated with different users such that each device is used for different treatment programs. In some instances, the user devices 150a, 150b, 150c can additionally store an installed mobile application that enables the user devices to exchange communications with the publishing system 130 and receive a set of customization instructions that configure the interfaces 152a, 152b, and 152c.

Figure 2A:
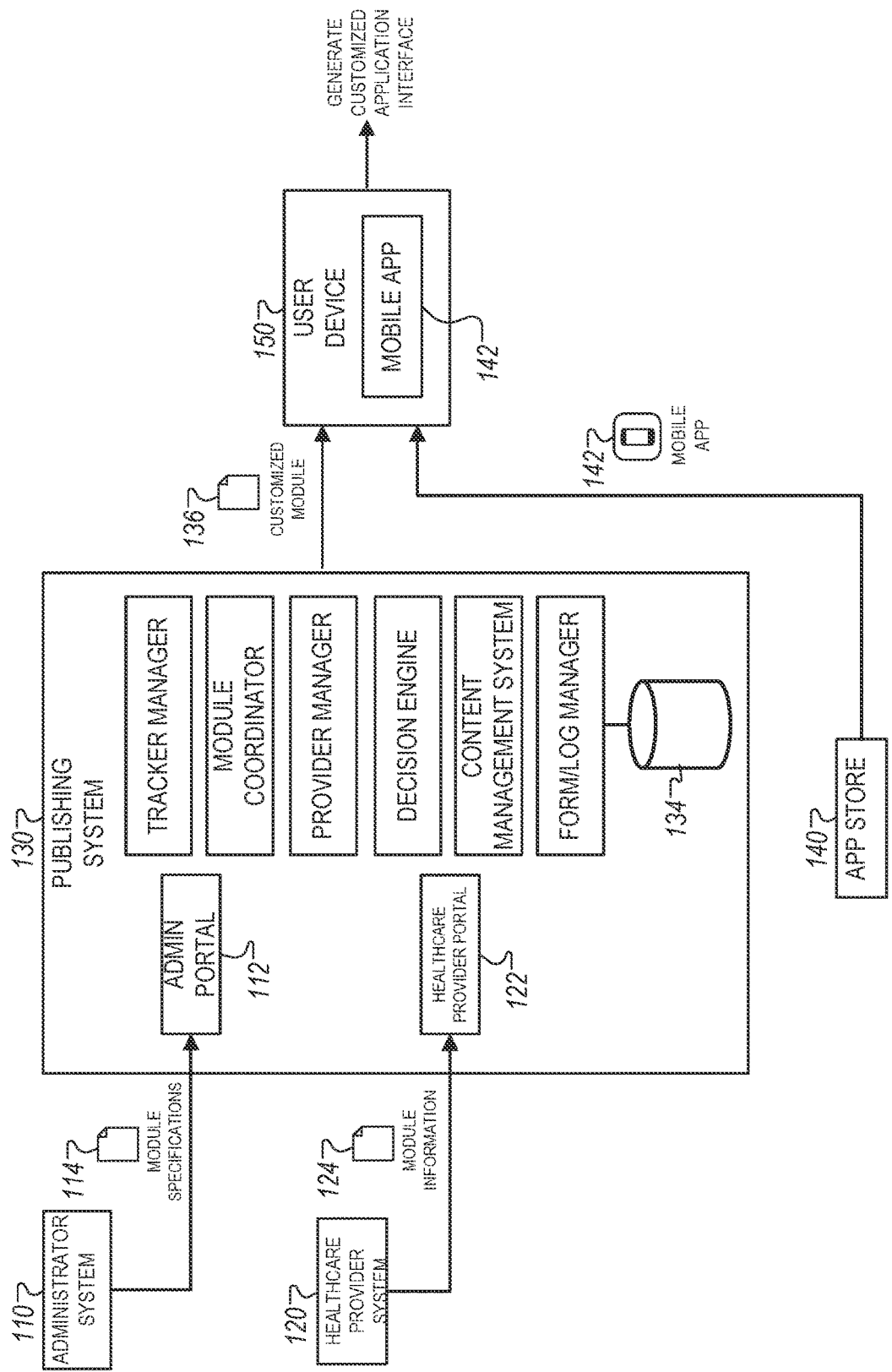
FIG. 2A is a diagram that illustrates an example of a process for publishing a customized module to a user device.

FIG. 2A is a diagram that illustrates an example of a process 200 for publishing a customized health management module to a user device 150. In general, the process 200 can be used to customize health management modules based on health-related associated with particular treatment programs that a user of the user device 150 is enrolled in, health-related information submitted by providers, and module specifications created by a system administrator. In this regard, the process 200 can be used by a plurality of entities within an application ecosystem, as described with respect to FIG. 1, to provide a set of customized health management modules can include provider-specific, client organization-specific, and user-specific information to the user device 150.

The process 200 initially starts when the administrator system 110 transmits module specifications 114 to the publishing system 130. As described above, the module specifications 114 can include account information for client organizations, providers, and/or users, access control lists specifying account privileges for features associated with customized health management modules, or client organizational frameworks that link client organizations to a list of available providers and treatment programs that are offered to users. The module specifications 114 can be inputted and/or updated by an administrator using the admin portal 112 as described with respect to FIG. 1. In some implementations, the module specifications 114 can also include access credentials associated with a provider or a user. For example, the access credentials can be based on a code such as a value from a quick reader (QR) code, a personal identifier number (PIN), or a user-selectable password that is associated with the mobile application 142.

In addition to the administrator system 110 transmitting the module specifications 114, the healthcare provider system 120 transmits module information 122 to the publishing system 130. As described previously, the module information 122 can include health-related information associated with client organizations such as policy information for health insurance provides associated with an employer. The module information 122 can also include a list of providers that accept the particular types of health insurance provided to employees by an employer. In some instances, the module information 122 can include client organization-specific information that is used to customize the appearance of the health management modules for the client organization. For example, in such instances, the module information 122 can include proprietary information, marketing or branding information associated with the organization, healthcare initiatives that are offered by the client organization, or treatment programs that are offered as services by associated providers to the users. In each of these examples, the module information 122 is used to gather client organization-specific information that is then used to generate a customized health management module that includes published information that is unique to the client organization.

After receiving the module specifications 114 and the module information 122, the publishing system 130 can execute a set of computer-implemented procedures to generate the customized module 136. For instance, the publishing system 130 can include a set of dedicated software modules that perform a set of particular actions based on the data submitted on the administrator portal 112 and the healthcare provider portal 122.

As depicted in FIG. 2A, the publishing system 130 can include a tracker manager that creates and manages trackers associated with treatment programs provided to users based on data submitted on the healthcare provider portal 122. For example, the trackers can monitor treatment milestones for a patient undergoing recovery after an operation based on the type of procedure performed.

The publishing system can also include a module coordinator that processes operations related to multiple customized health management modules for a provider or a client organization. For instance, the module coordinator can assign relative importance to individual health management modules such that certain health management modules that provide life-critical information to users can be prioritized over recreational health management modules. In other instances, the module coordinator can create and adjust update schedules for individual health management modules that determine how often each of the individual health management modules are periodically customized.

The module coordinator can also process incoming signal transmissions from different components of the publishing system 130 and generate instructions to perform particular activities by the publishing system 130. For instance, the module coordinator can receive module-specific content from the content manager and determine instructions to generate a customized health management module that includes the module-specific content. The module coordinator can additionally receive module-specific protocols, which can be used to adjust how customized health management modules are displayed on the user device, and/or implement security features that are used to protect personally identifiable information associated with users.

The publishing system 130 also includes a provider manager that monitors activities of multiple providers that are available for each organization. For instance, the provider manager can receive a list of providers for each client organization from the administrator system 110 and then monitor incoming and outgoing transmissions from the program coordinator. For example, the module coordinator can provide information related to a specific treatment program, and the provider manager can then determine the appropriate provider for the treatment program.

The publishing system 130 also includes a decision engine that executes computer-implemented processes based on one or more rules associated with configuration protocols of the health management modules. For instance, the decision engine can extract configuration data from the module specifications 114 transmitted from the administrator system 110, compare the extracted configuration data to a set of business rules specified within the admin portal 112, and execute responsive operations based on the comparison. For example, the decision engine can determine appropriate content to be included within a customized healthcare module, select the appropriate content and transmit the content selection to the content manager. In another example, the decision engine can determine a set of configuration protocols based on information included within the module specifications 114, and transmit the set of configuration protocols to the program coordinator.

The publishing system 130 also includes a content management system (CMS). The CMS stores content items for different modules and specifies how particular content items are used in health management modules. The CMS may store and organize any of the components of a module template or a completed module. For example, the CMS may store text, media, and other content that is used to form module templates made available by the publishing system 130. This stored information may also include descriptions of particular user interactions for a module, user experiences provided by a module, or characteristics of user interfaces. The CMS may also store custom content provided by organizations when they customize module templates to generate a customized module, for example, text, logos, images, videos, and so on. Other examples of content that can be stored by the CMS include messages to be displayed to a user, hyperlinks, files, or email templates.

The content management system can categorize content items according to the type of content or the intended usage of the content. The intended usage can indicate what portion of an interface of a module the content should be displayed, or when the content should be presented during use of a module. Some items may be categorized for display on a main content panel, while other items may be designated for display on a settings panel, a reminder view, a calendar view, or other portion of an interface. Content items in the CMS may be designated for display in response to certain conditions, such as surveys or forms to be provided in response to certain actions. Similarly, the CMS may include preloaded provider messages, such as pre-defined content that a healthcare provider may be able to cause to be displayed when appropriate.

The publishing system 130 also includes form/log manager that maintains a set of customized forms created in the admin portal 112. The forms are used to gather data such as user-submitted information, user preferences, and/or other user inputs that include health-related information associated with the provider or the client organization. For instance, the forms or logs can include patient surveys that request healthcare-related information from patients prior to a medical consult. In other instances, the forms or logs can include module-specific content such as treatment information or prescription dosages. In addition, the forms can include various user interface components that are associated with particular data types entered by the user (e.g., field entry fields for user-submitted text queries, user-specific graphical content, provider-lists populated for a particular client organization, etc.).

The form/log manager can also execute a set of computer-implemented instructions received from the module configurator. For instance, the instruction can include logic for selecting particular user interface components and adjusting the layout of user interface components on a particular user form/log based on the operations performed by the module coordinator. In this regard, the data transmissions between the module coordinator and the format/log manager enables the generation of user forms that can customize the layout of user interface components, transitions between different sections or user interface components, and/or specify one or more conditions for generating specific types of user forms. In one example, in response to determining that the user has an upcoming checkup with a primary care provider, the module coordinator transmits instructions to the form/log manager to generate a user form that includes relevant clinical information and appointment information. In response to receiving the instructions, the form/log manager can generate a patient checkup form that includes the user data received from the module manager. In addition, the form/log manager can customize the display and layout of the user data such that the most vital patient information is displayed in a more central location of the user form than other non-vital patient information.

After processing the data included within the module specifications 114 and the module information 124 and performing the operations described above, the publishing system 130 can store processed data within the repository 134 and generate a set of customized module 136. As described previously with respect to FIG. 1, the repository 134 can include historical user data, templates for stored health management modules for generation on the user device 150 at a later time period, components or rules generating customized health management modules, and/or lists of applicable health management modules for particular user devices based on user, provider, and client organization information.

The customized module 136 can provide a user interface displayed on the mobile application 142 that includes published information based on the module specifications 114 and the module information 124. For instance, as depicted in FIG. 5C, the customized module 136 can include client organization-specific information (e.g., logos and promotional material) and information submitted by a healthcare provider (e.g., clinical information for the user). In some examples, the customized module 136 can displayed on the mobile application 142 by adjusting the display of the interface of the mobile application 142 by publishing information received by the publishing system 130.

After a module 136 has been received from the publishing system 130, the module 136 may be updated in a manner that is seamless and transparent to the user. The mobile application 142 can obtain updates to the module 136 from the publishing system 130 in real-time, e.g., in the background while the user is interacting with the module. The application 142 may incorporate updates to the customized module 136 so that the module 136 and the interface shown at the user device 150 are updated without requiring the user to re-login into the mobile application 142. Similarly, updates may occur without any update to the mobile application 142 from the app store 140. For example, in some instances, the customized module 136 can be locally stored on the user device 150. The user may have the application 142 open and in use, showing the interface of the module 136. While user is interacting with the interface, the application 142 may request an update from the publishing system 130, or the publishing system 130 may push an update to the application 142. When an update is received, the interface and interactivity of the module 136 may be updated, even by changing aspects of the current view shown to the user.

In some implementations, the customized module 136 can also include one or more computer-implemented protocols for generating customized health management modules for display on the user device 150. For instance, the customized module 136 can specify content to be displayed based on user, healthcare provider, and client organization information, designate a layout for the specified content based on user-specific settings, and/or provide user-specific information such as a list of providers for the client organization associated with the user. The data can be provided by a provider entity 102b on the provider portal interface 122.

In some instances, the customized module 136 can also specify a set of conditional rules that enable the user to track health-related information on customized health management modules that are generated on the user device 150. The set of conditional rules can be used to trigger the display of tracking information and reminders associated with a treatment program that the user is registered in, and execution of other actions performed on the user device 150. An example of a conditional rule can be automatically adjusting the list of providers that are displayed on a customized health management module based on determining that the user is scheduled to have a particular procedure performed as a part of a treatment program. In such an example, the list of providers displayed includes providers that support healthcare-related services associated with the particular procedure (e.g., post-operative recovery and monitoring, follow-up procedures, etc.).

After receiving the customized module 136, the user device 150 generates the customized health management modules based on implementing module specifications included within the customized module 136 as described previously.

In some implementations, as depicted in FIG. 2A, the customized health management modules can be generated by the mobile application 142. As described previously, the mobile application 142 can be installed from the app store 140 for the corresponding operating system of the user device 150. The mobile application 142 can initially be configured to include a set of baseline health management modules when the mobile application 142 is first installed on the user device 150. The baseline health management modules include generalized content and content layout that can be adjusted based on the customized module 136. For instance, the generalized content can be basic information associated with the system 100 that is applicable to all providers, client organizations, and users (e.g., user authentication protocols, mobile application infrastructure, system configurations and settings, etc.). In this regard, the customized module 136 can be used to adjust the baseline health management modules to display entity-specific information and exhibit user and provider-specific interaction settings such that the front-end user interface of the mobile application 142 appears unique to each user that operates on a single application framework.

Figure 2B:
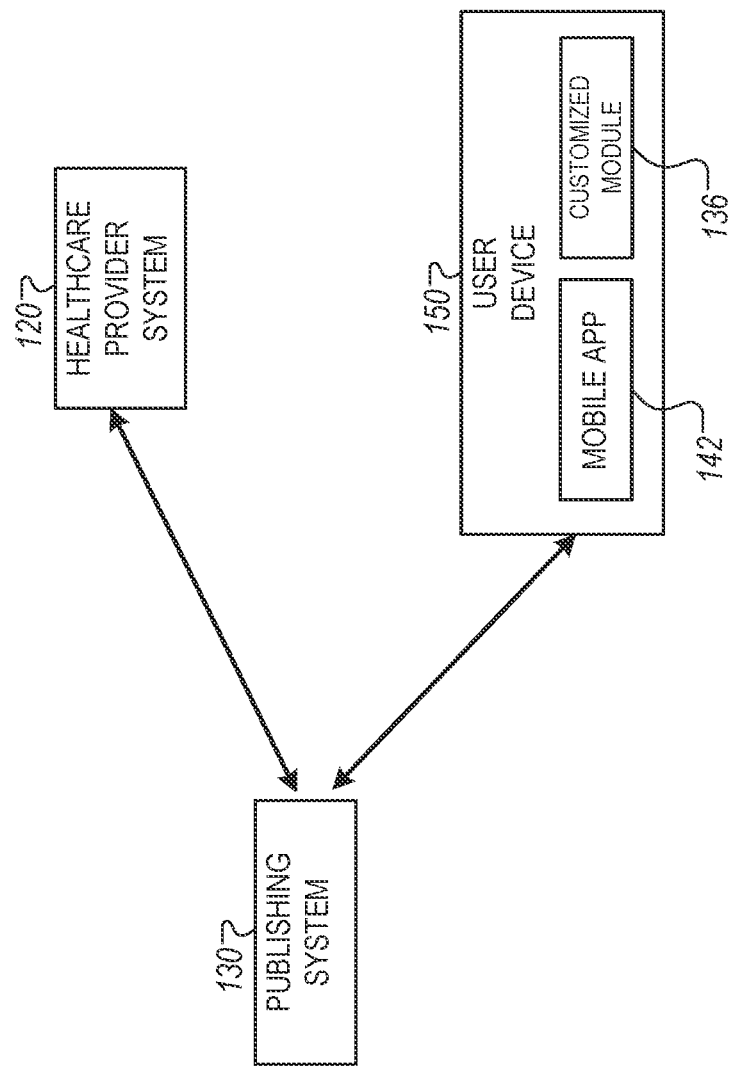
FIG. 2B is a diagram that illustrates communication that a publishing system facilitates between various systems.

FIG. 2A is a diagram that illustrates communication that the publishing system 130 facilitates between various systems. Once the customized module 136 is installed at the user device 150, the publishing system 130 facilitates communication between the user and healthcare providers. The same publishing system 130 from FIG. 2A is shown in FIG. 2B for convenience, but this system may represent multiple server systems or a different server system from the one that generates or provides the customized module 136 in FIG. 2A.

In some implementations, the publishing system 130 enables two-way asynchronous or synchronous communication between users of the module 136 and healthcare providers associated with the module 136. For example, users may submit questions for a doctor through an interface of the module 136, and the doctor may respond through an interface of the module 136, or vice versa. As another example, after a user has entered information, for example, indicating symptoms, exercise activity, or whether medicine was taken, the information may be uploaded to the publishing system 130 and made available to the healthcare provider. As another example, a healthcare provider may send content to be displayed within the interface of a module 136, e.g., educational materials, surveys, a predefined or customized message, and so on. Thus the healthcare provider may encourage or instruct a user of a module 136 remotely through the publishing platform. Messages can be provided through notifications, even when the application 142 and module 136 are not active on the user device 150. As another example, messages can be shown when a user opens the application 142, navigates to a particular view of the module 136, or opens a message inbox of the module 136. In some implementations, a module 136 may permit a live chat or video conference between a user and a healthcare provider.

In some implementations, healthcare providers can use the publishing system 130 to monitor or observe patients on an ongoing basis. These features can facilitate real-time messaging and real-time remote care planning. As noted above, customized modules can include trackers that specify types of information to obtain and provide to the publishing system. The information may be provided periodically or in response to particular triggers or conditions. For example, a module focused on diabetes care may provide periodic updates about a patient's most recent blood sugar tests. As another example, a module supporting fitness may provide a notification when a certain level of activity has been detected by sensors of the user device 150. In some instances, healthcare providers may send requests, to the publishing system 130, for information about their patients on an on-demand basis, and the publishing system 130 communicates with an individual user device 150 to obtain and provide the requested information. In this regard, customized modules may define communications permissions, e.g., to specify what information is permitted to be collected by the module 136, and what healthcare providers can receive the information.

In some implementations, a module specifies how existing functionality of the application 142 is to be used. Unlike application updates, the addition of a module can be done without modifying the actual executable files of the application 142. Instead of altering the application 142, the module can indicate what existing functionality of the application 142 to expose to a user, and in what manner. For example, the application 142 may include functionality for tracking and analyzing various types of sensor data of a device. A module can define, from among the capabilities of the application 142, which data should be collected and at what frequency. Additionally, the module can specify rules for how to process acquired data, as well as actions that the user's device should perform conditioned on the analysis. Thus, a module can change the ongoing or default behavior of the application 142. A module can be persistent at a user's device, for example, stored and active until a user indicates that the module should be removed. In some implementations, modules adjust the initial view or behavior of the application 142, the content and interactions with a user while the application 142 is active, and/or actions performed by the application 142 in the background while a different application is active.

A module may be structured in a number of different formats. In some implementations a module is structured as XML data or other non-executable data, and in some instances excludes executable content. In some instances, a module may include executable or interpretable instructions. In some instances, a module includes references to other content, and instructs the application 142 to download the additional content to support the module. The module may specify that additional content should be downloaded, e.g., when the module is first installed, or that additional information should be obtained or refreshed on a periodic or ongoing basis, or that additional information should be downloaded on-demand when the user accesses certain views or when certain triggering conditions are detected by the application 142.

As discussed above, a module can represent a combination of a template and customization settings. The content of the module may include various different items, including user interface instructions (e.g., defining formatting, size, color, layout, media displayed, etc.), branding (e.g., an organization's name, logo, colors, contact info), organization-specific information (e.g., identifying an applicable health insurance plan). Modules can include tracker components, such as data that defines a trigger or condition to cause a particular type of data to be collected, as well as actions to take when the trigger occurs (e.g., send to a server, store, analyze, notify user, etc.). Modules may define a set of user experiences, such as interaction flows or dialogs for a user, or forms, surveys, games, or other interactions. The module may include media content, and additionally or alternatively include links to media provided by one or more other sources, such as servers. The module can provide educational materials, information about specific medical conditions, and treatment regimens or wellness plans. The information provided through a module, and the interactions that the module instructs the application 142 to provide to the user, can be based on clinically-validated health or treatment information. As noted above, installing a module can configure the application 142 in various ways, including specifying how the application 142 accesses sensor data, provides user interface elements, interacts with an operating system or other applications (e.g., configuring the application 142 to send reminders, messages, notifications at device), and interacts over a network.

In some implementations, modules include information that connects a user device to healthcare providers. For example, the module can configure the application 142 to provide information (e.g., sensor data of the phone, user comments, health plan compliance information) to a physician, coach, or other health care provider. This information may be sent from a user's device through the publishing server to a device of the provider. Similarly, a module may configure the application 142 so that, through the publishing platform, the healthcare provider can send real-time communications or updates to treatment plans or goals. According to the instructions in the module, communications from providers can be displayed or used to modify the interactions of the application 142 with the user.

Figure 3:
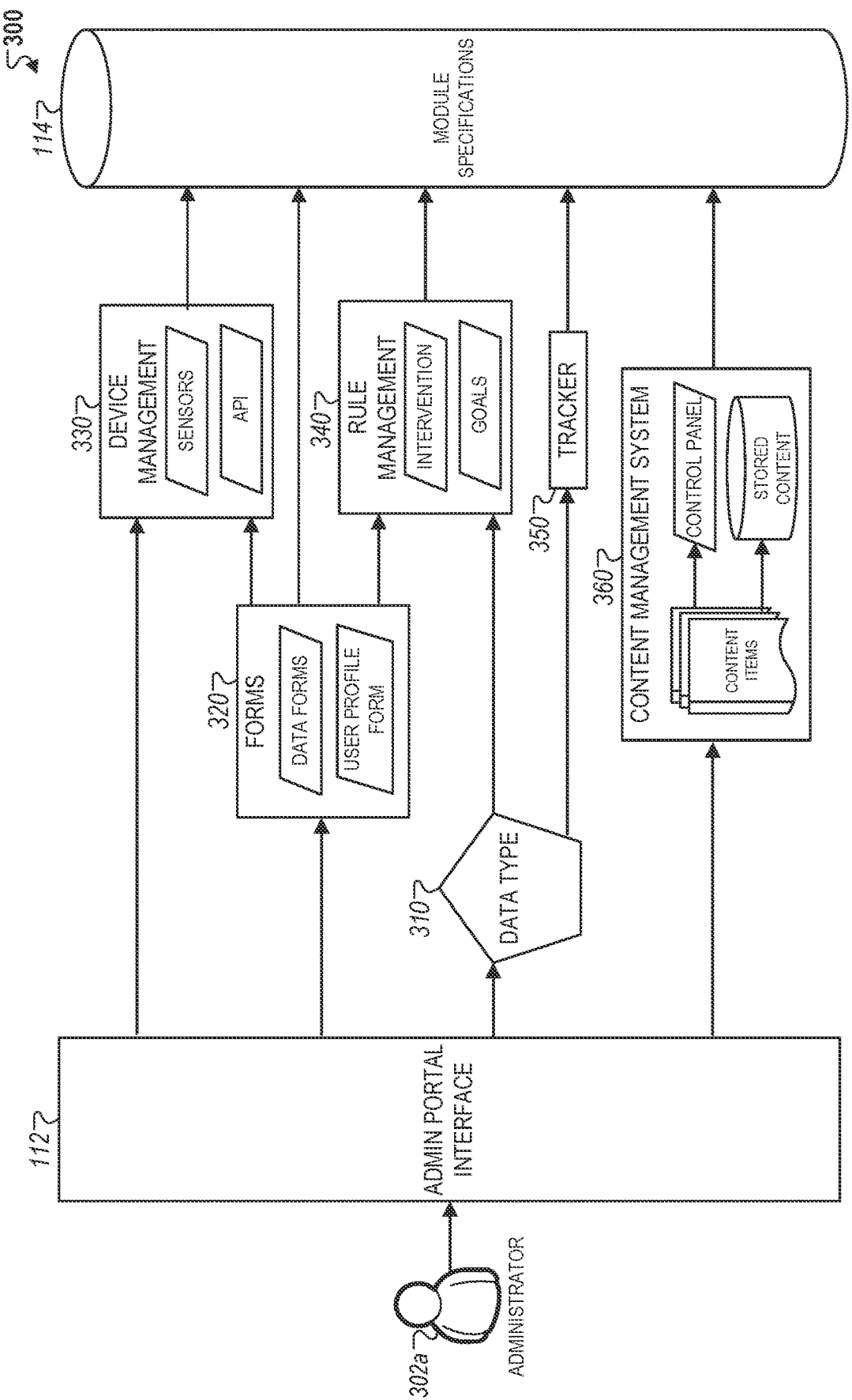
FIG. 3 is a diagram that illustrates examples of data that can be used to generate module specifications for a customized health management module.

FIG. 3 is a diagram that illustrates examples of data that can be used to generate module specifications for a customized health management module. The data can be provided by an administrator 302a on the admin portal 112. Briefly, the data provided by the administrator 302a can include a data type 310, form information 320, device management information 330, rule management information 340, tracker information 350, and/or content information from a content management system 360.

In general, the various types of data provided by the administrator 302a can be processed sequentially or parallel in order to generate the module specifications 114. For instance, aggregation techniques can be used such that data from multiple sources can be cross-correlated to generate a single output (e.g., the module specifications 114). For example, as depicted in FIG. 3, information submitted on forms 320, such as user demographic information submitted on data forms and the user's healthcare plan information on a user profile form be combined to specifically manage a user device associated with the user (e.g., perform specific authentication protocols associated with the user's health insurance provider). The form information 320 can also be used to specify rules related to intervention and wellness goals based on user-submitted information within the user profile form (e.g., utilizing a user's indication of lifestyle choices to adjust the behavior of the system 100 based on detecting wellness data associated with the user activities.

In more detail, the data type 310 is used to keep track of user-submitted information on the mobile application 142. For instance, the data type 310 can include a category associated with the user-submitted information that indicates how the user-submitted information should be processed by the system 100. For example, user inputs indicating a user's health-related information can be categorized as categorical data to determine user privileges whereas user inputs including symptoms can be categorized as treatment-related data that is provided to applicable providers associated with a treatment program that the user is currently enrolled in.

The form information 320 includes user-submitted information on forms such as user registration forms, inpatient forms, or patient surveys. As depicted in FIG. 3, two examples of forms can include data forms where a user submits inputs that are used as activity data associated with the user. For example, data forms can include forms for tracking exercise activity for wellness monitoring purposes. The other example can include a user profile form, which includes demographic information, user preferences, and health-related information such as a healthcare plan, or other clinically relevant information (e.g., medical history, immunization records, etc.).

The rule management information 340 specifies conditions that designate how particular types of user data are processed, and specific actions to be taken by the system 100 based on received user data. As depicted in FIG. 3, two examples of rules can include interventions where user data on forms can be used to predict at-risk conditions associated with the user and provide alerts on the health management modules to provide information related to preventative measures to present the at-risk conditions. For example, a user's medical history indicating risks of high blood pressure can be combined with sensor information from a heart rate sensor to predict the risk of a heart attack. In the second example, user goals can be determined based on a set of user preferences provided by the user on the user profile form. For example, a user can submit information related to an exercise regimen on the user profile form, which can be used to set of personal wellness goals that are periodically updated and communicated through notifications on the health management modules.

The trackers 350 are used to monitor user data from multiple sources and transmit signals in response to detecting patterns associated with the monitored user data. For instance, the trackers 350 can be used to monitor specific biometric parameters (e.g., heart rate, blood pressure, oxygen levels) in related to a user's healthcare conditions to adjust the activity of the system 100. For example, as described previously, the health management modules can be customized to display pertinent healthcare-related information. In this example, the trackers 350 can transmit signals to adjust the information displayed on the health management modules based on real-time biometric measurements. The trackers 350 can also designate conditions or contexts that trigger measurement and measuring of particular types of user information.

The content management system 360 is used to specify how particular content items to be displayed on the health management modules are processed by the system 100. As depicted in FIG. 3, the content management system 360 may either process content to adjust settings within a control panel or stored in a repository. For example, the content management system 360 can categorize content items' intended usage by the users or by types of content. In the first instance, the intended usage can be used to adjust particular settings in the control, or generate preloaded messages from providers that are associated with the intended usage. In the second instance, content items can be classified as, for example, messages, hyperlinks, files, or email templates.

The control panel can be used to adjust one or more settings related to the display of content within the health management modules. For example, the control panel can specify which particular content items are associated with particular health management modules, particular users, or rule-based events. In another example, the control panel can specify how content items are presented within a health management module (e.g., design layouts, or transition effects).

Figure 4:
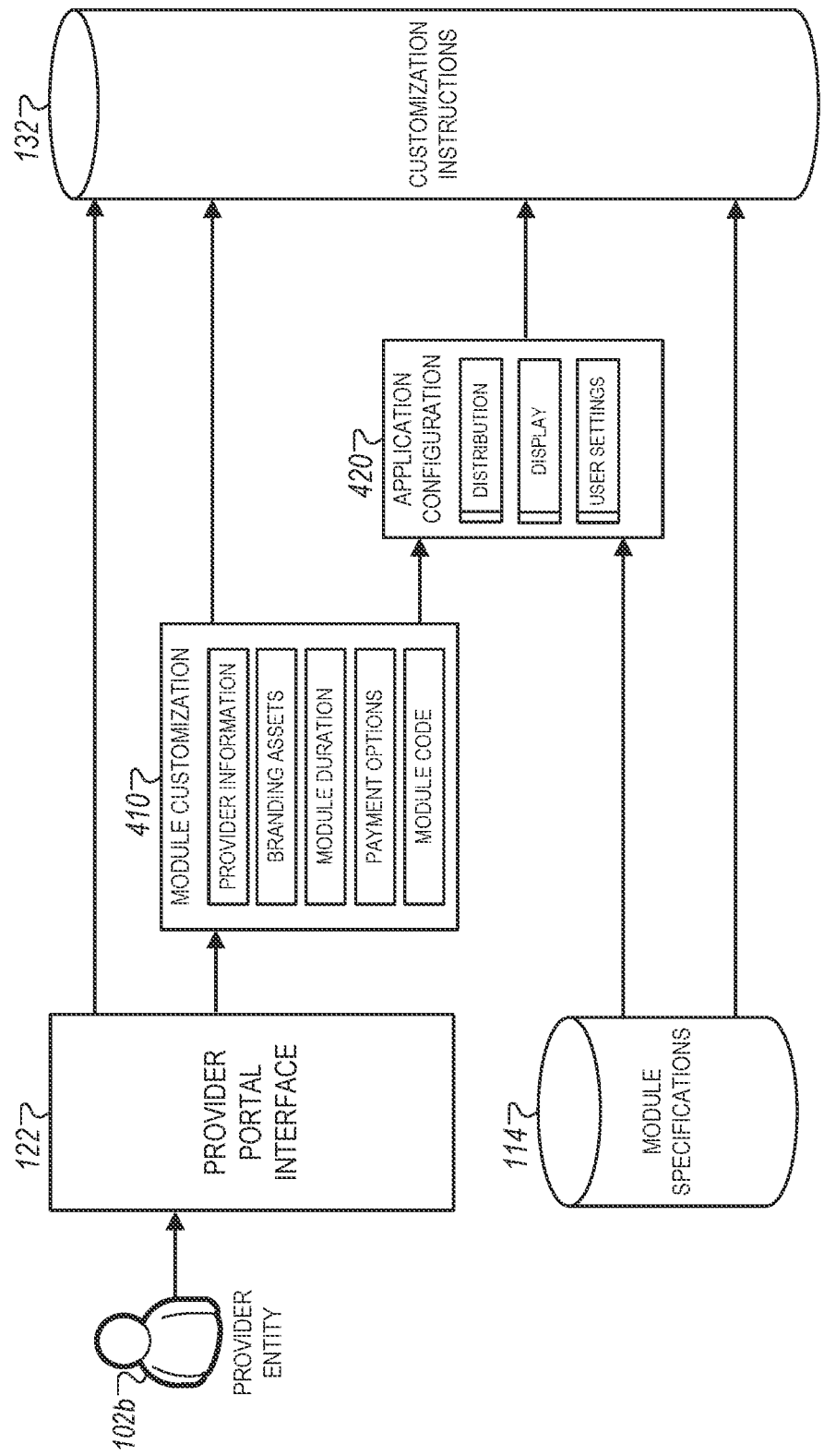
FIG. 4 is a diagram that illustrates examples of data that can be used to generate customization instructions for a customized health management module.

FIG. 4 is a diagram that illustrates examples of data that can be used to generate customization instructions for a customized health management module. The data can be provided by a provider entity 102b on the healthcare provider portal 122. Briefly, the data provided by the provider entity 102b can include module customization information 410 and application configuration 420. The data provided by the provider 102b can further be combined with the module specifications 114, as described previously, in order to generate the customization instructions 132.

In general, provider-specific information can be submitted on the provider portal interface 122 in order to customize the display of the health management modules on user devices of users that are associated with the provider. In some instances, the provider entity 102b can be a client organization such as an employer. In this regard, the module customization information 410 and the application configuration 420 is eventually combined with the module specifications 114 to generate the customization instructions 132.

In more detail, the module customization information 410 includes provider-specific information that are used to adjust the display and layout of content, graphics, and/or other information on the health management modules. As depicted in FIG. 4, examples of module customization information 410 can include provider information, branding assets, module duration, payment information, and module code. Provider information can include areas of practice, types of health insurances accepted, and/or size of healthcare practices. Branding assets can include marketing or promotional content (e.g., logos, advertisements, program incentives, etc.) that are specific to the provider entity 202a.

The module duration specifies how long a health management module will be displayed on the user device 150. For example, health management modules for short-term conditions (e.g., a doctor's appointment) can be accessible for one day whereas modules for chronic disease treatment programs (e.g., a weight management program) can be accessible for extended periods until the user has achieved goals associated with the treatment program. The payment options indicate methods of payment that are accepted by the provider entity 102b and specified amounts charged for procedures performed (e.g., co-pay amounts for checkups). The module code includes provider-specific numbers, associated with procedures, billing codes, and/or other accounting information, used to identify healthcare services provided to users.

The application configuration 420 can be one or more settings associated with the mobile application 142 that adjust how the health management modules 142 are displayed on the mobile application 142. As depicted in FIG. 4, examples of application configurations 420 can include application distribution (e.g., how the mobile application 142 is provided to users), application display (e.g., workflow design of the mobile application 142), and user settings (e.g., user-submitted preferences that configure the mobile application 142). The application configuration 420 is generated based on aggregating the module specification 114 and the module customization 410 using similar techniques as those described with respect to FIG. 3.

Figure 5A:
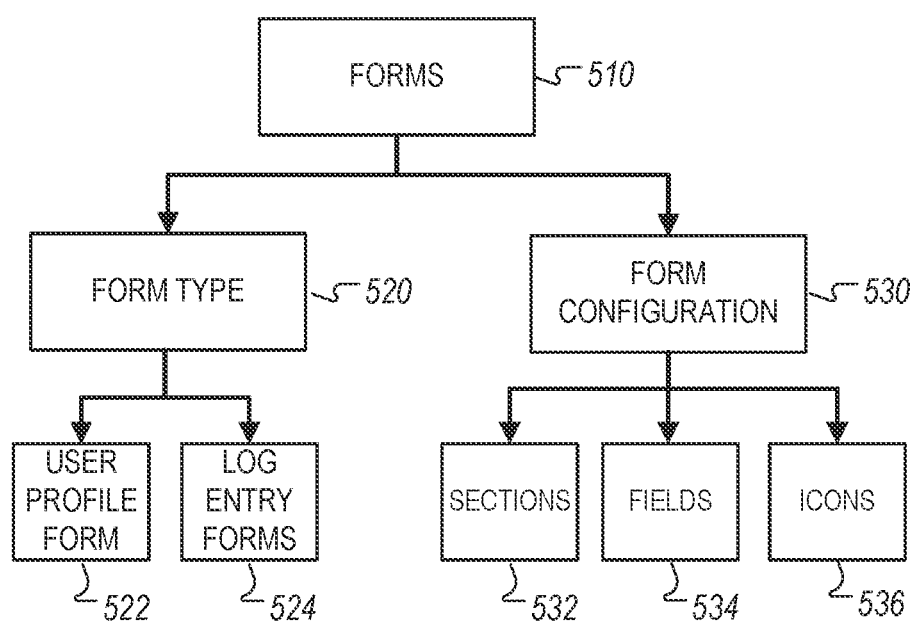
FIGS. 5A-5B are diagrams that illustrate examples of customization instructions for a published customized module.
Figure 5B:
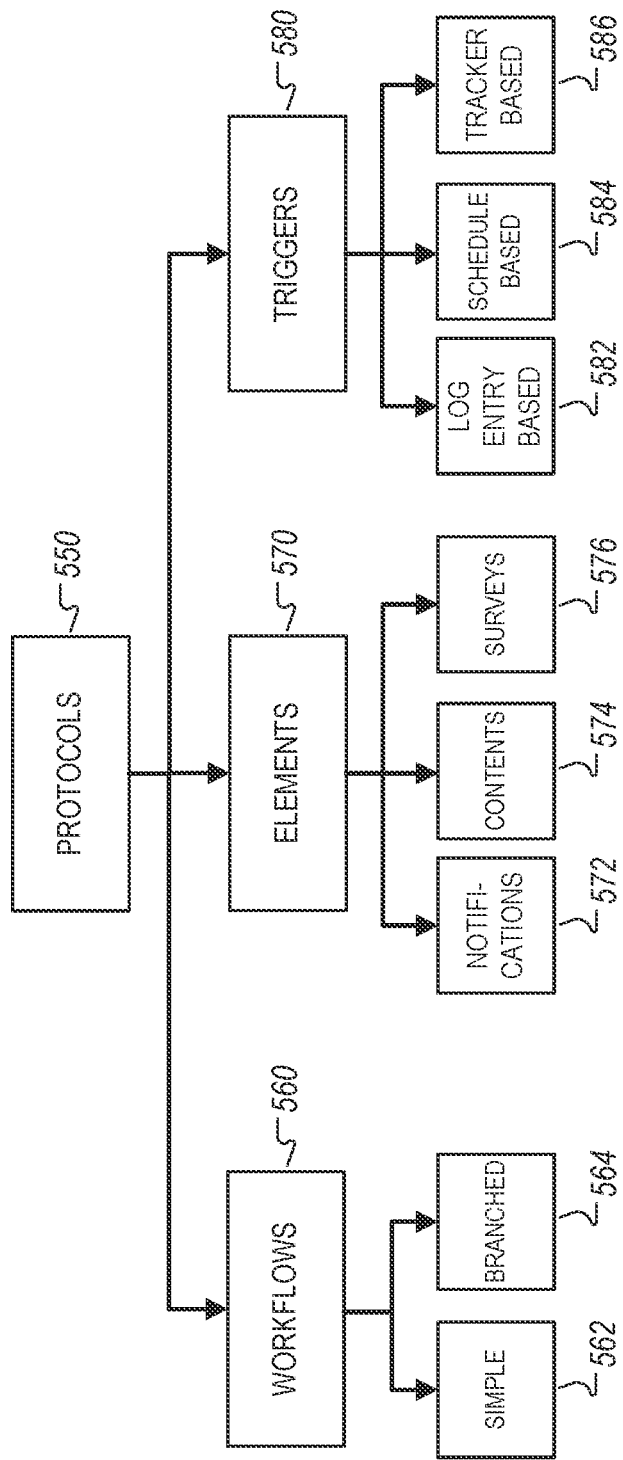
Figure 5C:
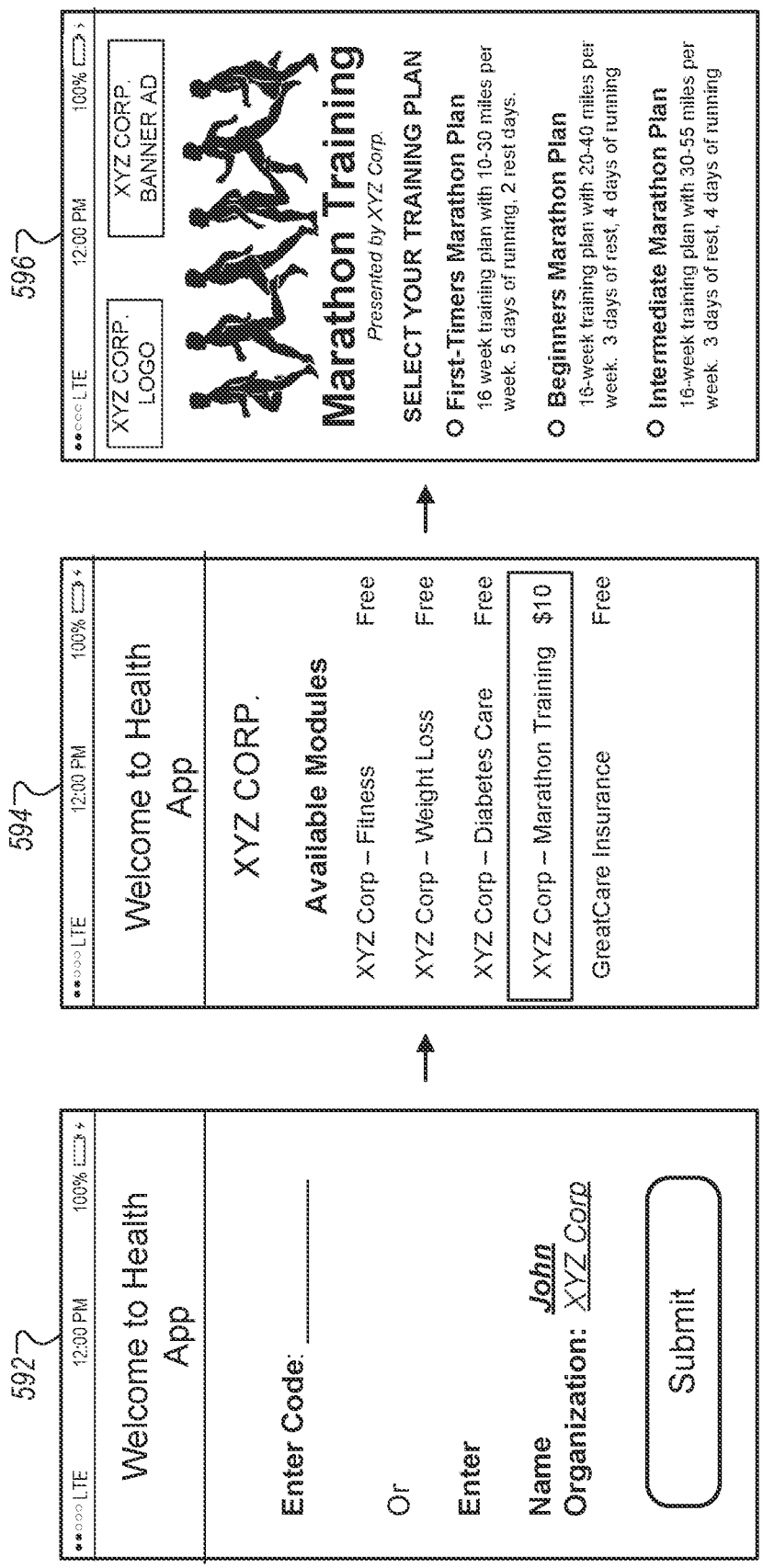
FIG. 5C is a diagram that illustrates an example of user interfaces for selecting a customized module.

FIGS. 5A-5B are diagrams that illustrate examples of customization instructions for generating customized health management modules. FIG. 5A depicts examples of customization instructions that can be generated based on information selected from user forms 510. FIG. 5B depicts examples of customization instructions that can be generated based on different adjustment protocols.

Referring to FIG. 5A, examples of information selected from forms 510 can be form type 520 and form configuration 530. The form type 520 refers to a category assigned to a particular form based on the nature of information included within the particular form. Examples of form types can include a user profile form 522 that requests a user to provide demographic insurance information, and a log entry form 524 that includes data that is used to measure user activity in relation to a treatment program that the user may be registered in. The form configuration 530 refers to an arrangement and presentation of components included within the form 510. Examples of form configurations can include sections 532, fields 534, and icons 536. The sections 532 refer to the individual areas of the form 510 that organize different types of user information. The fields 534 refer to different types of data fields that enable the user to provide field submissions that describe user information.

The icons 536 refer to various graphical content that can be associated with providers and client organizations that are associated with the user.

Referring to FIG. 5B, examples of adjustment protocols can be workflows 560, elements 570, and triggers 580. The workflows 560 refer to data aggregation techniques used to propagate user data from multiple sources to generate the customized module 136. Examples of workflows 560 include a simple workflow 562 where user data is aggregated using a linear process using a preconfigured algorithm and a branched workflow 564 where user data is aggregated based on a set of decision points that specify different aggregation techniques for each result of the decision point. For instance, as described previously, rules or conditions can be used to analyze characteristics of user data and perform conditional processes that are designed to be more appropriate for the characteristics of the user data. For example, in some instances, scores representing characteristics of user data can be compared to threshold values to determine the result at a decision point.

The elements 570 refer to different interface elements of the health management modules. Examples of the elements 570 include notifications 572, content 574, and surveys 576. The notifications 572 can be alerts that are provided to users or providers in response to detecting alarm events associated with detected user data, or periodic updates that provide a user's progress within a treatment program. For example, the notifications 572 can be calorie loss alerts that are associated with a weight loss program). The content 574 can be user information or data that is included within the health management modules. For example, the content 574 can be data visualizations for monitored activity data, text fields that include a user's account information, or user input fields that enable a user to submit information that may be relevant to the treatment program. The surveys 576 can be different types of user forms that request information from the user to determine a user's progress within a treatment program. For example, the surveys 576 can include patient response surveys that allow a user to provide pain severity scores during a medical consult to provide information related to symptoms that the user may be experiencing.

The triggers 580 refer to different types of conditions that initiate a set of computer-implemented processes related to the health management modules.

Examples of the triggers 580 include log entry based triggers 582, schedule based triggers 584, and tracker based triggers 586. The log entry based triggers 582 initiate processes in response receiving user inputs that match a set of specified conditions. For example, a log entry based trigger can initiate a communication session on the health management modules between a provider and a user based on receiving user input indicating that the user may require emergency medical assistance. The schedule based triggers 584 initiate processes on a reoccurring basis based on a specified schedule associated with user data provided on the health management modules. For example, a schedule based trigger can trigger a display of a daily calorie intake for the user based on times that are associated with the user's exercise regimen. The tracker based triggers 586 initiate processes based on monitoring user data and determining that the monitored user data satisfies one or more conditions associated with the monitored data. For example, a tracker-based trigger may track heart rate data and in response to detecting an elevated heart rate above a threshold value, transmit instructions to the update exercise data that is presently displayed on the healthcare management module.

FIG. 5C depicts examples of interfaces 592, 594, and 596 on the mobile application 142. Briefly, the interface 592 displays an initial landing page of the mobile application, which may be displayed after the user installs the application. On interface 592, a user can provide information associated with a particular client organization or customized module to obtain information about available modules. The interface 594 displays a list of available health modules for the particular client organization allowing a user to select an appropriate module. The interface 596 displays a customized health module that has been selected by the user, downloaded to the user's device, and used to customize the experience of the application for a particular client organization.

In more detail, the interface 592 can initially be displayed on the mobile application 142 once the user first runs the mobile application 142 on the user device 150. As depicted, the user can provide information such as a code that is associated with a particular client organization, or identifying information such as a name of the user and the name of the client organization. In these examples, the user-submitted information is provided to the publishing system 130, so that the publishing system 130 can retrieve and return a list of available health modules corresponding to the particular code or the particular client organization that the user indicated. In the example shown, the user indicates that he is an employee of XYZ corp, and the user submits this information to the publishing system 130.

The interface 594 displays a gallery of available health modules for a particular client organization, e.g., "XYZ CORP" in the example. In addition, the interface 594 presents a list of available modules that are associated with XYZ CORP and with a healthcare provider that is associated with XYZ CORP (e.g., GreatCare Insurance). The available health modules can have pricing options available that are specified by the particular client organization. For example, the module for marathon training includes a ten dollar fee for access. A user can then make a selection of one of the available modules, which then directs the user to the interface 596.

In the example, the user selects the marathon training module on the interface 594, and the module is downloaded to the user's device. As a result, the mobile application customizes its interface to display the information and features specified by the customized module. The interface 596 is an example of an interface of the mobile application after processing the customized health module. The interface 596 can include client organization-specific information such as logos, or marketing and promotional materials. The interface 594 can also display information provided by a healthcare provider associated with the client organization. In the example, marathon training information such as various skill levels for a user, different training regimen for each skill level represents information that is provided by a healthcare provider associated with the XYZ CORP.

In some implementations, instead of entering information about an organization, a user may obtain information about a module by entering a code that is associated a particular module or a particular set of modules. For example, the publishing system 130 may store a table that associates modules with codes corresponding to the modules. An organization may distribute the code for a particular module, e.g., by an e-mail, SMS text message, a web page, or other means. At the interface 592, the user may enter the received code to be taken directly to an interface showing information for a specific module (or specific set of modules). For example, an employer may distribute a code that, when entered into the appropriate field of interface 592 and submitted, brings the user directly to a view describing and making available the customized module for the employer. In some implementations, submitting the code may cause the application 142 to automatically download and install the corresponding module. In some implementations, the code may be provided in a hyperlink or other interactive element that a user can interact with to cause a user device to then automatically open the application 142, submit the code, and either download or show information about a particular module.

In some implementations, the code is used to verify a user's authorization to obtain a module. For example, in addition to providing information associated with the organization on the interface 592, the user can also be asked to provide an authentication code on the interface 594 in order to gain access to an available module for the organization. For example, the authentication code can be provided to users that purchase a subscription service of the organization.

In addition, the available modules that are displayed on the interface 594 can be adjusted based on a permission level associated with the user of the mobile application. For example, the available modules can be associated with age requirements such that if a user attempts to access a particular module with a higher age requirement, the application can restrict access to the particular module. In other examples, the permission levels can also be based on a user classification (e.g., role within an organization) or a different types of purchased subscriptions for healthcare services.

Figure 5D:
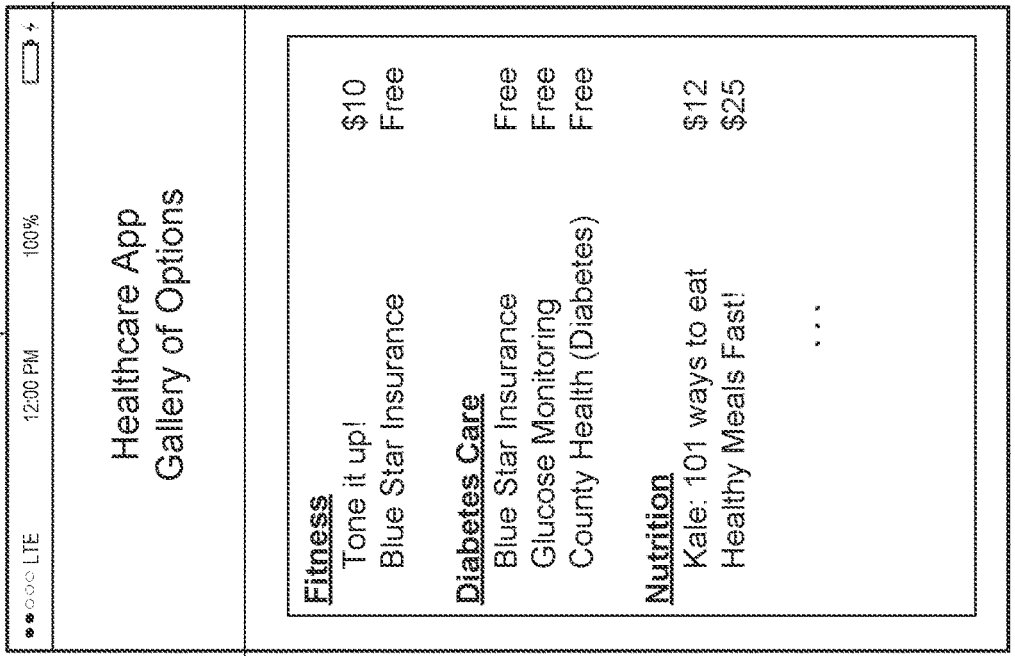
FIG. 5D is a diagram that illustrates an example of a user interface for selecting modules available to a user.

FIG. 5D is a diagram that illustrates an example of a user interface 598 for selecting modules. The interface 598 shows a gallery of different types of modules that are available. For example, the gallery may show a marketplace of modules that are published by the publishing system 130, but which have been customized by various different organizations. These organizations can provide modules that are sold through the publishing platform.

The interface 598 may be shown to any user of the application 142, allowing the user to browse and select one or more modules. As illustrated, the interface 598 may show a gallery or marketplace view showing different categories of available modules. These may be categorized by, for example, medical condition or aspect of wellness addressed by the module, popularity, price, or organization type or organization that is offering the module through the platform.

Figure 6A:
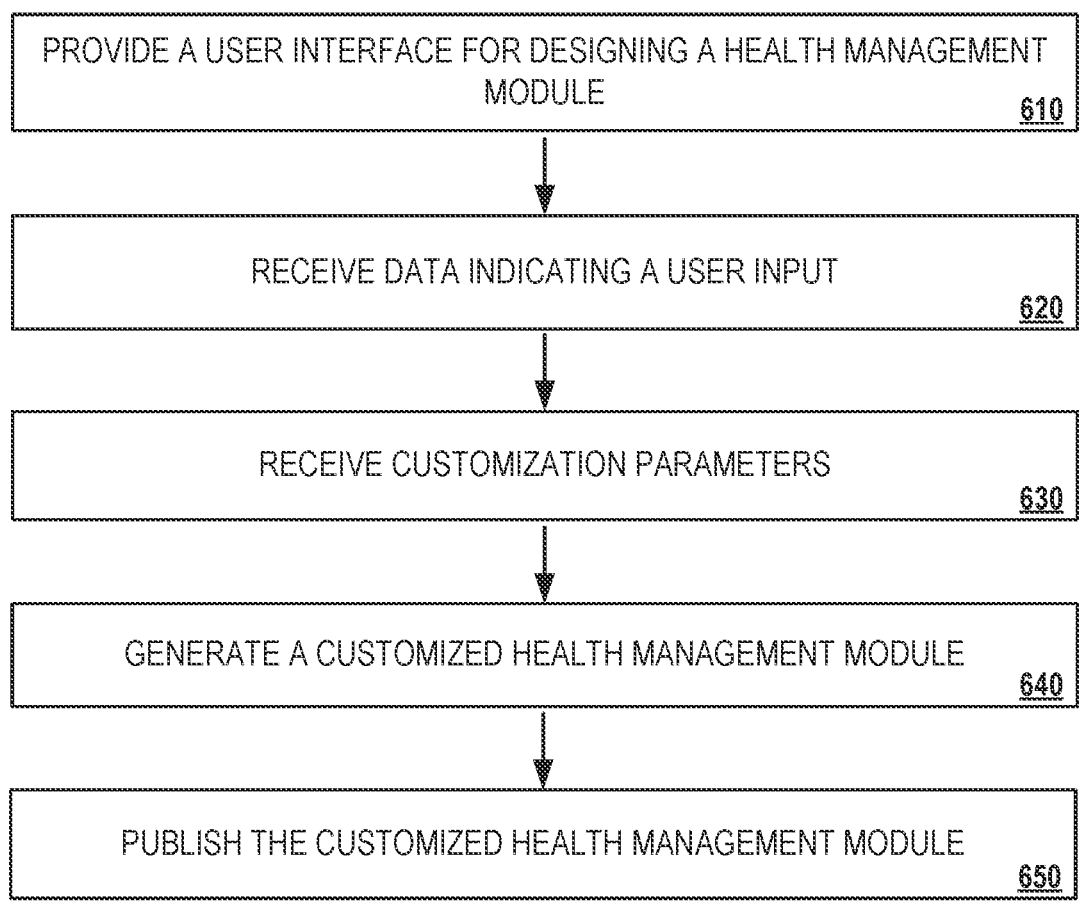
FIGS. 6A-6B are diagrams of examples of processes for publishing a customized module.
Figure 6B:
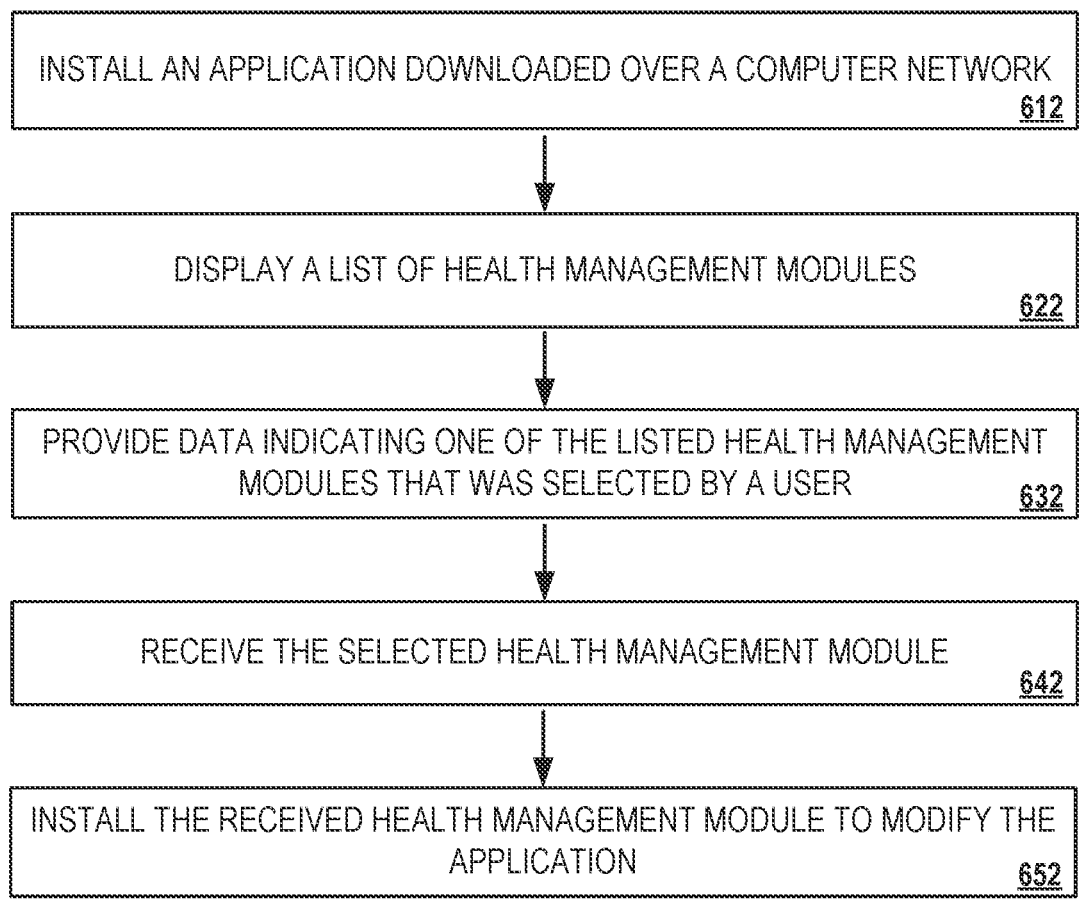

FIG. 6A-6B are diagrams of example of processes 600A-600B for publishing customized health management modules. Referring to FIG. 6A, the process 600A can include providing a user interface for designing a health management module (610), receiving data indicating a user input (620), receiving customer parameters (630), generating a customized health management module (640), and publishing the customized health management module (650).

In more detail, the process 600A can include providing a user interface for designing a health management module (610). For instance, the publishing system 130 can provide the admin portal 112 for designing a health management module. The admin portal 112 can identify a plurality of health management module templates such as the module specifications 114. As described previously, the healthcare management templates can include account information associated with client organizations or user access privileges for particular client organizations or users, and other related information available on the admin portal 112. In addition, the publishing system 130 can also provide the healthcare provider portal 122 for specifying provider information associated with the health management module.

The plurality of health management module templates can include templates corresponding to treatment programs for different treatment programs. For example, as described previously, the plurality of health management module templates can include a set of templates associated with health and wellness programs targeted to improve fitness and another set of templates associated with chronic disease treatment targeted to assist users to recover from treatment procedures. In some instances, the templates indicate treatment recommendations and/or other types of clinically relevant information sent from the provider, tutorials targeted to assist the user, or billing codes associated with specific procedures performed on the user. In other instances, the plurality of templates includes a set of interactivity settings that specify a set of user actions to follow, which types of user forms and surveys to include in the health management module, and when to present the user forms and surveys. In addition, the set of interactivity settings can also define how the mobile application 142 uses the customized health module 136 and a set of instructions that direct how the mobile application 142 interacts with the user.

In some implementations, the user interface for the health management module can be provided as a webpage that includes the user interface. For instance, as described previously, a browsing application on can be used to access the webpage and identify the plurality of health management module templates.

The process 600A can include receiving data indicating a user input (620). For example, the publishing system 130 can receive data indicating a user input from an administrator through the admin portal 112. The user input can include a selection of one of the plurality of health management module templates.

The process 600A can include receiving customization parameters (630). For instance, the customization parameters can initially be generated based on aggregating data included within the module specifications 114 and the module information 124, and then transmitted the customization parameters to the publishing system 130. As described previously, the customization parameters can be used to customize the selected module template for a particular client organization.

In some implementations, the customization parameters can include provider and/or client organization-specific information include links to health insurance networks or lists of healthcare providers that are supported by a client organization that generates the health management module for the user. As described previously, the provider-specific information can include images, names, logos, or other types of marketing and promotional materials associated with a brand of the provider or client organization. In other implementations, customization parameters can update trackers 350 to indicate what information should be transmitted to the user and a time point when the information should be transmitted. The customization parameters can also specify access conditions associated with the information shown in the health management module, or custom health-related goals, initiatives, or contests sponsored by the client organization. The access conditions can specify individuals that can have sufficient privileges to view information shown in the health management module, or specific circumstances where an individual can access the information. For example, the access conditions can provide privileges to view the information that are conditioned upon the occurrence of one or more detected events associated with the individual.

The process 600A can include generating a customized health management module (640). For instance, the publishing system 130 can generate a customized health management module for the particular client organization based on the selected template and the customization parameters.

The process 600A can include publishing the customized health management module (650). For instance, the publishing system 130 can publish the customized health management module on the user device 150 for display to a user. The customized health management module can include the customized module 136 that configures the mobile application 142 on the user device 150. As described previously, the mobile application 142 can be provided by a third-party application store such as the app store 140.

In some implementations, the publishing system 130 may make the customized health management modules accessible over the network 105 for access by the mobile application 142 on the user device 150. As described previously, the mobile application 142 can be installed on the user device 150 from the app store 140 and afterwards the mobile application 142 can receive data transmissions from the publishing system 130 that include the customized health management modules. In some instances, the publishing system 130 can also provide an index of available modules to the mobile application 142 or search results indicating relevant modules for search criteria associated with the modules. For example, a user can provide search criteria for a particular treatment program on the mobile application 142, and in response the publishing system can provide the search results indicating the relevant modules that include one or more features associated with the particular treatment program.

In some instances, in addition to making the customized health management modules accessible over the network 105 for the mobile application 142, the publishing system 130 can also transmit a set of instructions such that the customized health management modules change the operation of the mobile application 142 on the user device 150. For example, the set of instructions can enable the customized health management modules adjust the visual attributes of the mobile application 142, provide notifications associated with the customized healthcare modules, or enable the customized health management modules to interact with existing components of the mobile application 142.

Referring now to FIG. 6B, the process 600B can include installing an application downloaded over a computer network (612), displaying a list of health management modules (622), providing data indicating one of the listed health management modules that was selected by a user (632), receiving the selected health management module (642), and installing the received health management module to modify the application (652).

In more detail, the process 600B can include installing an application downloaded over a computer network (612). For instance, a user can install the mobile application 142 on the user device 150 from the app store 150. The mobile application 142 can be downloaded over the network 105 from a content provider server.

The process 600B can include displaying a list of health management modules (622). For instance, after installing the mobile application 142 on the user device 150, the user device 150 can display a list of health management modules provided by the publishing system 130. As described previously, the publishing system 130 is independent of the content provider server of the app store 140.

The process 600B can include providing data indicating one of the listed health management modules that was selected by a user (632). For instance, the publishing system 130 can provide data to the user device 150 indicating one of the listed health management modules that was selected by the user of the user device 150.

The process 600B can include receiving the selected health management module (642). For instance, the user device 150 can receive the selected health management module. In some instances, the received health management module is the customized health module 136 as depicted with respect to FIG. 2A.

The process 600B can include installing the received health management module to modify the application (652). For instance, the user device 150 can install the received health management module to modify the mobile application 142 to interact with the user according to the received health management module. As an example, the display of the user interface of the mobile application 142 can be adjusted based on the received health management module so that user can view client organization-specific information that is included within the received health management module.

The techniques discussed above may be used for generating, publishing, updating, and managing customized modules for many different purposes. For example, while various examples discussed herein refer to healthcare management modules, customized modules may be generated and published for uses outside the healthcare area.

Figure 7:
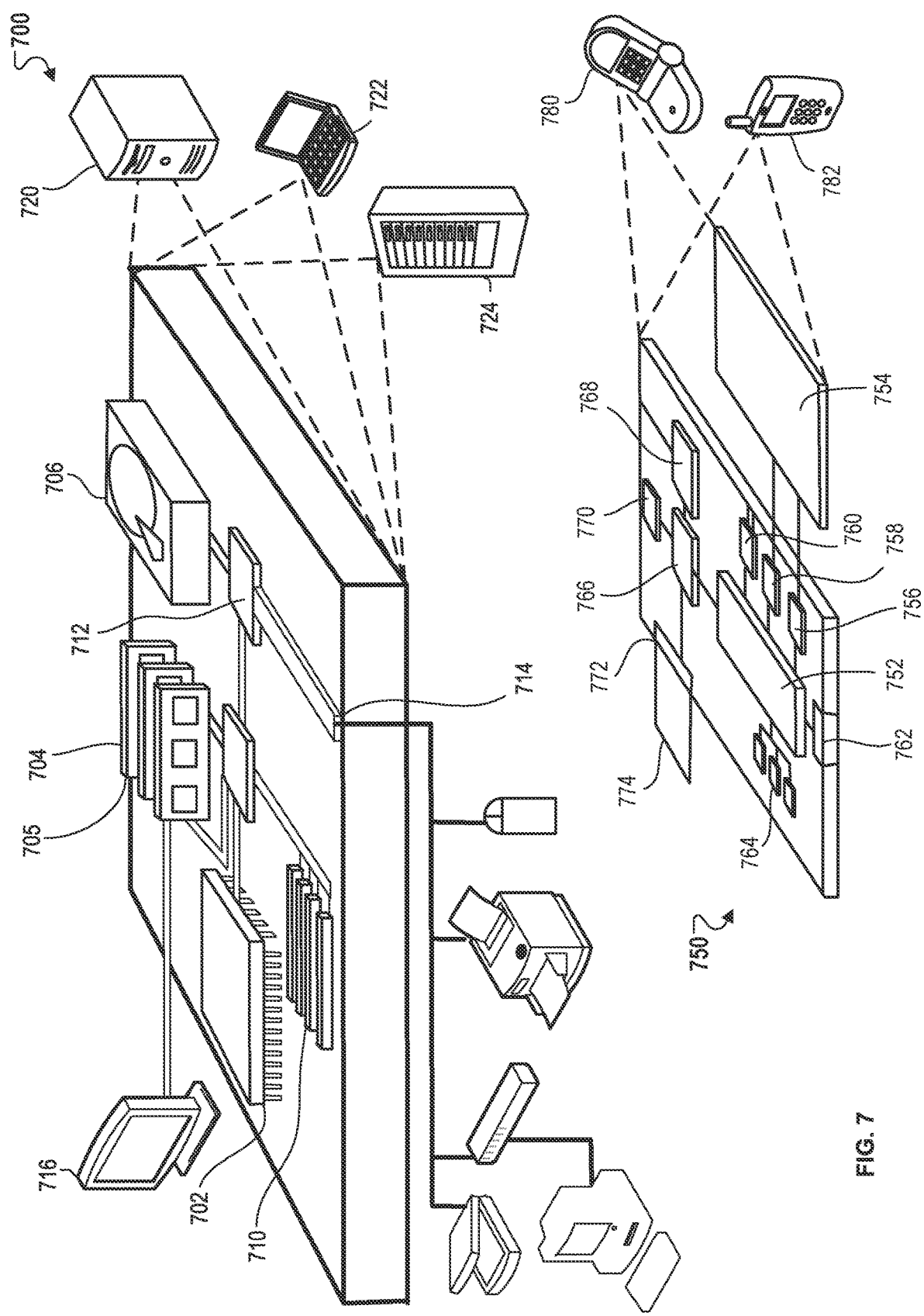
FIG. 7 is a block diagram of computing devices on which the processes described herein, or portions thereof, can be implemented.

FIG. 7 is a block diagram of computing devices 700, 750 that can be used to implement the systems and methods described in this document, as either a client or as a server or plurality of servers. Computing device 700 is intended to represent various forms of digital computers, such as laptops, desktops, workstations, personal digital assistants, servers, blade servers, mainframes, and other appropriate computers. Computing device 750 is intended to represent various forms of mobile devices, such as personal digital assistants, cellular telephones, smartphones, and other similar computing devices. Additionally, computing device 700 or 750 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 700 includes a processor 702, memory 704, a storage device 706, a high-speed interface 708 connecting to memory 704 and high-speed expansion ports 710, and a low speed interface 712 connecting to low speed bus 714 and storage device 706. Each of the components 702, 704, 706, 708, 710, and 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as display 716 coupled to high speed interface 708. In other implementations, multiple processors and/or multiple buses can be used, as appropriate, along with multiple memories and types of memory. Also, multiple computing devices 700 can be connected, with each device providing portions of the necessary operations, e.g., as a server bank, a group of blade servers, or a multi-processor system.

The memory 704 stores information within the computing device 700. In one implementation, the memory 704 is a volatile memory unit or units. In another implementation, the memory 704 is a non-volatile memory unit or units. The memory 704 can also be another form of computer-readable medium, such as a magnetic or optical disk.

The storage device 706 is capable of providing mass storage for the computing device 700. In one implementation, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 704, the storage device 706, or memory on processor 702.

The high speed controller 708 manages bandwidth-intensive operations for the computing device 700, while the low speed controller 712 manages lower bandwidth intensive operations. Such allocation of functions is exemplary only. In one implementation, the high-speed controller 708 is coupled to memory 704, display 716, e.g., through a graphics processor or accelerator, and to high-speed expansion ports 710, which can accept various expansion cards (not shown). In the implementation, low-speed controller 712 is coupled to storage device 706 and low-speed expansion port 714. The low-speed expansion port, which can include various communication ports, e.g., USB, Bluetooth, Ethernet, wireless Ethernet can be coupled to one or more input/output devices, such as a keyboard, a pointing device, microphone/speaker pair, a scanner, or a networking device such as a switch or router, e.g., through a network adapter. The computing device 700 can be implemented in a number of different forms, as shown in the figure. For example, it can be implemented as a standard server 720, or multiple times in a group of such servers. It can also be implemented as part of a rack server system 724. In addition, it can be implemented in a personal computer such as a laptop computer 722. Alternatively, components from computing device 700 can be combined with other components in a mobile device (not shown), such as device 750. Each of such devices can contain one or more of computing device 700, 750, and an entire system can be made up of multiple computing devices 700, 750 communicating with each other.

The computing device 700 can be implemented in a number of different forms, as shown in the figure. For example, it can be implemented as a standard server 720, or multiple times in a group of such servers. It can also be implemented as part of a rack server system 724. In addition, it can be implemented in a personal computer such as a laptop computer 722. Alternatively, components from computing device 700 can be combined with other components in a mobile device (not shown), such as device 750. Each of such devices can contain one or more of computing device 700, 750, and an entire system can be made up of multiple computing devices 700, 750 communicating with each other.

Computing device 750 includes a processor 752, memory 764, and an input/output device such as a display 754, a communication interface 766, and a transceiver 768, among other components. The device 750 can also be provided with a storage device, such as a microdrive or other device, to provide additional storage. Each of the components 750, 752, 764, 754, 766, and 768, are interconnected using various buses, and several of the components can be mounted on a common motherboard or in other manners as appropriate.

The processor 752 can execute instructions within the computing device 750, including instructions stored in the memory 764. The processor can be implemented as a chipset of chips that include separate and multiple analog and digital processors. Additionally, the processor can be implemented using any of a number of architectures. For example, the processor 710 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 750, such as control of user interfaces, applications run by device 750, and wireless communication by device 750.

Processor 752 can communicate with a user through control interface 758 and display interface 656 coupled to a display 754. The display 754 can be, for example, a TFT (Thin-Film-Transistor Liquid Crystal Display) display or an OLED (Organic Light Emitting Diode) display, or other appropriate display technology. The display interface 656 can include appropriate circuitry for driving the display 754 to present graphical and other information to a user. The control interface 758 can receive commands from a user and convert them for submission to the processor 752. In addition, an external interface 762 can be provide in communication with processor 752, so as to enable near area communication of device 750 with other devices. External interface 762 can provide, for example, for wired communication in some implementations, or for wireless communication in other implementations, and multiple interfaces can also be used.

The memory 764 stores information within the computing device 750. The memory 764 can be implemented as one or more of a computer-readable medium or media, a volatile memory unit or units, or a non-volatile memory unit or units. Expansion memory 764 can also be provided and connected to device 750 through expansion interface 762, which can include, for example, a SIMM (Single In Line Memory Module) card interface. Such expansion memory 764 can provide extra storage space for device 750, or can also store applications or other information for device 750. Specifically, expansion memory 764 can include instructions to carry out or supplement the processes described above, and can include secure information also. Thus, for example, expansion memory 764 can be provide as a security module for device 750, and can be programmed with instructions that permit secure use of device 750. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 764, expansion memory 764, or memory on processor 752 that can be received, for example, over transceiver 768 or external interface 762.

Device 750 can communicate wirelessly through communication interface 766, which can include digital signal processing circuitry where necessary. Communication interface 766 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 768. In addition, short-range communication can occur, such as using a Bluetooth, Wi-Fi, or other such transceiver (not shown). In addition, GPS (Global Positioning System) receiver module 660 can provide additional navigation- and location-related wireless data to device 750, which can be used as appropriate by applications running on device 750.

Device 750 can also communicate audibly using audio codec 660, which can receive spoken information from a user and convert it to usable digital information. Audio codec 660 can likewise generate audible sound for a user, such as through a speaker, e.g., in a handset of device 750. Such sound can include sound from voice telephone calls, can include recorded sound, e.g., voice messages, music files, etc. and can also include sound generated by applications operating on device 750.

The computing device 750 can be implemented in a number of different forms, as shown in the figure. For example, it can be implemented as a cellular telephone 480. It can also be implemented as part of a smartphone 682, personal digital assistant, or other similar mobile device.

Various implementations of the systems and methods described here can be realized in digital electronic circuitry, integrated circuitry, specially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method performed by one or more computers, the method comprising:
   storing, by the one or more computers, modules that are respectively configured to customize monitoring performed by an application, wherein at least some of the modules are configured to cause different items to be monitored by the application;
   providing, by the one or more computers, a module to a client device over a communication network, wherein the module is configured to enable a third-party system to initiate data collection from devices that have the application installed and that have received and processed the module;
   after the module is provided to the client device and has been received and processed by the client device, receiving, by the one or more computers, a request from the third-party system to collect information from the client device, wherein the request is provided over the communication network;
   in response to receiving the request from the third-party system, communicating, by the one or more computers, with the client device over the communication network to cause the client device to use elements from the module previously received and processed by the client device to (i) obtain the information requested by the request from the third-party system and (ii) transmit the obtained information to the one or more computers over the communication network; and
   providing, by the one or more computers, the obtained information from the client device to the third-party system over the communication network.

2. The method of claim 1, wherein the third-party system is a healthcare provider system.

3. The method of claim 1, wherein the stored modules include modules for different third-party systems, such that at least some of the modules are customized to cause the application to enable communication with different third-party systems.

4. The method of claim 1, wherein the stored modules include different modules for different sets of healthcare providers, such that each of the different modules is customized to cause the application to enable communication between users of the application and the set of healthcare providers corresponding to the module.

5. The method of claim 1, wherein providing the module to the client device comprises providing a module configured to cause the application to provide two-way asynchronous or synchronous communication between a user of the client device and one or more healthcare providers corresponding to the module.

6. The method of claim 1, wherein receiving the request from the third-party system to collect information from the client device comprises receiving a request from the third-party system to collect health information for a particular user;
   wherein communicating with the client device over the network comprises obtaining, from the client device of the particular user, the requested health information for the particular user in response to the request; and
   wherein providing the obtained information comprises providing the obtained health information for the particular user to the third-party system in response to the request.

7. The method of claim 1, wherein the module provided to the client device is configured to enable the application to present content provided by the third-party system; and
   wherein the method includes:
      receiving, from the third-party system over the communication network, a message for a user of the client device; and
      providing the message to the client device over the communication network for presentation to the user in the application.

8. The method of claim 1, wherein at least some of the modules are configured to enable different healthcare providers to monitor health of users through the application;
   wherein the module provided to the client device enables a particular set of healthcare providers associated with the third-party system to remotely monitor health of a user of the client device on an ongoing basis; and
   wherein the module provided to the client device includes content to configure the application to monitor particular types of health information and provide the health information periodically or in response to predetermined triggers or conditions.

9. The method of claim 1, wherein the module provided to the client device is configured to cause the application to:
   capture health data for a user of the client device;
   detect an event based on the captured health data; and
   provide a notification of the event to the one or more computers over the communication network over the communication network; and
   wherein the method includes, based on the received notification of the event, providing information about the event to the third-party system.

10. The method of claim 1, wherein the module specifies permissions including (i) a set of information that is permitted to be collected by the application when using the module and (ii) a set of recipients authorized to receive the information generated as directed by the module.

11. The method of claim 1, wherein providing the obtained information to the third-party system comprises providing obtained information comprising at least one of sensor data from the client device, comments of a user of the client device, or health plan compliance information.

12. The method of claim 1, wherein the module includes content to configure the application to receive communications or updates to treatment plans or goals for a user of the client device.

13. The method of claim 1, wherein the module includes content to configure the application to modify interactions of the application on the client device with a user of the client device based on communication from the third-party system.

14. The method of claim 1, wherein the module includes content to configure the application to enable chat or video conference communication between a user of the client device and one or more healthcare providers associated with the third-party system.

15. A system comprising:
one or more computers; and
one or more computer-readable media storing instructions that are operable, when executed by the one or more computers, to cause the one or more computers to perform operations comprising:
    storing, by the one or more computers, modules that are respectively configured to customize monitoring performed by an application, wherein at least some of the modules are configured to cause different items to be monitored by the application;
    providing, by the one or more computers, a module to a client device over a communication network, wherein the module is configured to enable a third-party system to initiate data collection from devices that have the application installed and that have received and processed the module;
    after the module is provided to the client device and has been received and processed by the client device, receiving, by the one or more computers, a request from the third-party system to collect information from the client device, wherein the request is provided over the communication network;
    in response to receiving the request from the third-party system, communicating, by the one or more computers, with the client device over the communication network to cause the client device to use elements from the module previously received and processed by the client device to (i) obtain the information requested by the request from the third-party system and (ii) transmit the obtained information to the one or more computers over the communication network; and
    providing, by the one or more computers, the obtained information from the client device to the third-party system over the communication network.

16. The system of claim 15, wherein the stored modules include modules that are respectively customized to cause the application to enable communication with a different third-party system.

17. The system of claim 15, wherein the stored modules include different modules for different sets of healthcare providers, such that each of the different modules is customized to cause the application to enable communication between users of the application and the set of healthcare providers corresponding to the module.

18. The system of claim 15, wherein providing the module to the client device comprises providing a module configured to cause the application to provide two-way asynchronous or synchronous communication between a user of the client device and one or more healthcare providers corresponding to the module.

19. The system of claim 15, wherein receiving the request from the third-party system to collect information from the client device comprises receiving a request from the third-party system to collect health information for a particular user;
    wherein communicating with the client device over the network comprises obtaining, from the client device of the particular user, the requested health information for the particular user in response to the request; and
    wherein providing the obtained information comprises providing the obtained health information for the particular user to the third-party system in response to the request.

20. One or more non-transitory computer-readable media storing instructions that are operable, when executed by one or more computers, to cause the one or more computers to perform operations comprising:
    storing, by the one or more computers, modules that are respectively configured to customize monitoring performed by an application, wherein at least some of the modules are configured to cause different items to be monitored by the application;
    providing, by the one or more computers, a module to a client device over a communication network, wherein the module is configured to enable a third-party system to initiate data collection from devices that have the application installed and that have received and processed the module;
    after the module is provided to the client device and has been received and processed by the client device, receiving, by the one or more computers, a request from the third-party system to collect information from the client device, wherein the request is provided over the communication network;
    in response to receiving the request from the third-party system, communicating, by the one or more computers, with the client device over the communication network to cause the client device to use elements from the module previously received and processed by the client device to (i) obtain the information requested by the request from the third-party system and (ii) transmit the obtained information to the one or more computers over the communication network; and
    providing, by the one or more computers, the obtained information from the client device to the third-party system over the communication network.

* * * * *